US009809522B2

(12) United States Patent
Smirnova et al.

(10) Patent No.: US 9,809,522 B2
(45) Date of Patent: Nov. 7, 2017

(54) SELECTIVE LIQUEFACTION OF LIGNIN AND BIOMASS IN A MIXTURE OF SUB- AND SUPERCRITICAL FLUIDS IN ABSENCE OR PRESENCE OF HETEROGENEOUS CATALYSTS

(71) Applicant: South Dakota Board of Regents, Pierre, SD (US)

(72) Inventors: Alevtina Smirnova, Rapid City, SD (US); Chris Lynde, Rapid City, SD (US); Abu Md Numan-Al-Mobin, Rapid City, SD (US); Rudresh Bommadihalli Rajappagowda, Rapid City, SD (US)

(73) Assignee: SOUTH DAKOTA BOARD OF REGENTS, Pierre, SD (US)

( * ) Notice: Subject to any disclaimer, the term of this patent is extended or adjusted under 35 U.S.C. 154(b) by 0 days.

(21) Appl. No.: 15/263,141

(22) Filed: Sep. 12, 2016

(65) Prior Publication Data

US 2017/0073291 A1   Mar. 16, 2017

Related U.S. Application Data

(60) Provisional application No. 62/217,558, filed on Sep. 11, 2015.

(51) Int. Cl.
| | |
|---|---|
| *C07C 45/00* | (2006.01) |
| *C07C 41/00* | (2006.01) |
| *C07C 41/18* | (2006.01) |
| *C07C 45/59* | (2006.01) |
| *C07C 27/00* | (2006.01) |

(52) U.S. Cl.
CPC .............. *C07C 41/18* (2013.01); *C07C 27/00* (2013.01); *C07C 45/59* (2013.01)

(58) Field of Classification Search
CPC ................. C07C 45/55; C07C 41/18
See application file for complete search history.

(56) References Cited

U.S. PATENT DOCUMENTS

| | | | |
|---|---|---|---|
| 7,365,236 B2 * | 4/2008 | Catallo | C10G 1/04 204/157.15 |
| 8,945,246 B2 | 2/2015 | Tsurutani et al. | |
| 8,968,479 B2 * | 3/2015 | Kilambi | C12P 7/10 127/44 |
| 2012/0060418 A1 * | 3/2012 | Epstein | B01J 23/462 48/127.7 |
| 2014/0154767 A1 | 6/2014 | O'Regan | |

FOREIGN PATENT DOCUMENTS

| | | |
|---|---|---|
| WO | 2010134077 A2 | 11/2010 |
| WO | 2011091044 A1 | 7/2011 |

OTHER PUBLICATIONS

Buzetzki, "Effects of oil type on products obtained by cracking of oils and fats", Fuel Processing Technology 92 (2011) pp. 2041-2047, Slovakia.
Carrier, "Conversion of fern (*Pteris vittata* L.) biomass from a phytoremediation trial in sub- and supercritical water conditions", "http://www.elsevier.com/locate/biombioe", Biomass and Bioenergy 35 (2011) pp. 872-883.
Chakinala, "Catalyst screening for the hydrothermal gasification of aqueous phase of bio-oil", Catalysis Today 195 (2012) pp. 83-92, Journal homepage: www.elsevier.com/locate/cattod, Netherlands.
Kang, "Hydrothermal conversion of lignin: A review", Renewable and Sustainable Energy Reviews 27 (2013), pp. 546-558, journal homepage: www.elsevier.com/locate/rser, China.
Cox, "Depolymerization of oak wood lignin under mild conditions using the acidic ionic liquid 1-H-3-methylimidazolium chloride as both solvent and catalyst", Bioresource Technology 118 (2012) pp. 584-588, journal homepage: www.elsevier.com/locate/biortech, USA.
Finch, "Catalytic hydroprocessing of lignin under thermal and ultrasound conditions", "www.elsevier.com/locate/cattod", Catalysis Today 196 (2012) pp. 3-10.
Firdaus, "Renewable co-polymers derived from vanillin and fatty acid derivatives", European Polymer Journal 49 (2013) pp. 156-166, journal homepage: www.elsevier.com/locate/europolj.
Gosselink, "Lignin depolymerisation in supercritical carbon dioxide/acetone/water fluid for the production of aromatic chemicals", Bioresource Technology 106 (2012) pp. 173-177, journal homepage: www.elsevier.com/locate/biortech.
Hofrichter, "Enzyme and Microbial Technology", "Review: lignin conversion by mananese peroxidase (MnP)" (2002), pp. 454-466, University of Helsinki, Finland.
Jessop, "Applications of CO2 in Homogeneous Catalysis", Div. Fuel Chem. 2004, vol. 49 pp. 1-6.
Konnerth, "Base promoted hydrogenolysis of lignin model compounds and organosolv lignin over metal catalysts in water", Chemical Engineering Science vol. 123 (2015), pp. 155-163, journal homepage: www.elsevier.com/locate/ces.
Lange, "Oxidative upgrade of lignin-Recent routes reviewed", European Polymer Journal 49 (2013), pp. 1151-1173, journal homepage:www.elsevier.com/locate/europolj, Italy.
Long, "Efficient base-catalyzed decomposition and in situ hydrogenolysis process for lignin depolymerization and char elimination", Applied Energy vol. 141 (2015) pp. 70-79, journal homepage: www.elsevier.com/locate/apenergy.
Ma, "Controlling the selectivity to chemicals from lignin via catalytic fast pyrolysis", Applied Catalysis A: General 423-424 (2012) pp. 130-136, journal homepage: www.elsevier.com/locate/apcata, Switzerland.
Ning, "Phenolic Materials via Ring-Opening Polymerization: Synthesis and Characterization of Bisphenol-A Based Benzoxazines and Their Polymers", Journal of Polymer Science: Part A; Polymer Chemistry, vol. 32, pp. 1121-1129, (1994), Ohio USA.

(Continued)

*Primary Examiner* — Sikarl Witherspoon
(74) *Attorney, Agent, or Firm* — Goodhue, Coleman & Owens, P.C.

(57) ABSTRACT

Disclosed herein are methods for selective synthesis of specific phenolic products by means biomass or biomass products liquefaction, manipulation of the said selectivity in favor of one specific phenolic compound or a mixture of specific phenolic compounds, and the synthesis of the phenolic compounds from a liquid or biomass organic fraction produced in presence of a homogeneous catalyst in supercritical state or a mixture of said homogeneous and one or several heterogeneous catalysts mixed with water in sub-critical, near-critical, or supercritical condition.

19 Claims, 17 Drawing Sheets

(56) References Cited

OTHER PUBLICATIONS

Parpot, "Biomass coversion: attempted electrooxidation of lignin for vanillin production", Jornal of Applied Electrochemistry 30: 727-731, 2000, Kluwer Acadamic Publishers, Netherlands.

Qian, "Structural analysis of bio-oils from sub-and supercritical water liquefaction of woody biomass", "www.sciencedirect.com", Energy vol. 32 (2007) pp. 196-202.

Saisu, "Conversion of Lignin with Supercritical Water-Phenol Mixtures", Energy & Fuels 2003, vol. 17, pp. 922-928.

Song, "Lignin depolymerization (LDP) in alcohol over nickel based catalysts", Energy & Environmental Science, 2013.

Sturgeon, "A Mechanistic Investigation of Acid-Catalyzed Cleavage of Aryl-Ether Linkages: Implications for Lignin Depolymerization in Acidic Envrionments", ACS Sustainable Chem. Eng. 2014, vol. 2 pp. 472-485.

Tabasinejad, "Water Solubility in Supercritical Methane, Nitrogen, and Carbon Dioxide: Measurement and Modeling from 422 to 483 K and Pressures from 3.6 to 134 MPa", Industrial & Engineering Chemistry Reseach, 2011, 50, pp. 4029-4041, American Chemical Society.

Tabasinejad, "Water Solubility in Supercritical Methane, Nitrogen, and Carbon Dioxide: Measurement and Modeling from 422 to 483 K and Pressures from 3.6 to 134 MPa", Industrial & Engineering Chemistry Research 2011, vol. 50, pp. 4029-4041.

Thring, "The production of gasoline range hydrocarbons from Alcell lignin using HZSM-5 catalyst", Fuel Processing Technology 62 (2000) pp. 17-30, Canada.

Toor, "Hydrothermal liquefaction of biomass: A review of subcritical water technologies", Energy 36 (2011) pp. 2328-2342, journal homepage: www.elsevier.com/locate/energy.

Valle, "Hydrothermally stable HZSM-5 zeolite catalysts for the transformation of crude bio-oil into hydrocarbons", Applied Catalysis B: Environmental 100 (2010) pp. 318-327, journal homepage: www.elsevier.com/locate/apcatb.

Vanholme, "Lignin Biosynthesis and Structure", American Society of Plant Biologists, 2010 vol. 153, pp. 895-905, www.plantphysiol.org, USA.

Wahyudion, Decomposition of lignin alkaline and chemicals recovery in sub- and supercritical water, (2004), Jumanoto University.

Wang, "Synthesis and copolymerization of fully bio-based benzoxazines from guaiacol, furfurylamine and stearylamine", www.rsc.org/greenchem (2012), vol. 14, pp. 2799-2806.

Yong, "Kinetic Analysis of Lignin Hydrothermal Conversion in Sub- and Supercritical Water", Industrial & Engineering chemistry Research 2013, vol. 52 pp. 5626-5639.

Yong, "Kinetic Analysis of Lignin Hydrothermal Conversion in Sub- and Supercritical Water", Industrial & Enineering Chemistry Research 2013, vol. 52, pp. 5626-5639, American Chemical Society.

Yong, "Reaction Kinetics of the Lignin Conversion in Supercritical Water", Industrial & Engineering Chemistry Research 2012, 51, pp. 11975-11988.

Yong, "Reaction Kinetics of the Lignin Conversion in Supercritical Water", Industrial & Engineering Chemistry Research 2012, vol. 51, pp. 11975-11988.

Yoshikawa, "Production of phenols from lignin via depolymerization and catalytic cracking", Fuel Processing Technology 108 (2013) pp. 69-75, journal homepage: www.elsevier.com/locate/fuproc, Japan.

Yoshikawa, "Production of Phenols from Lignin-derived Slurry Liquid using Iron Oxide Catalyst", Mar. 2014, pp. 1-41, Hokkaido University Collection of Scholarly and Academic Papers: HUSCAP.

Yoshikawa, "Production of phenols from lignin-derived slurry liquid using iron oxide catalyst", Applied Catalyst B: Environmental 146 (2014) pp. 289-297, journal homepage: www.elsevier.com/locate/apcatb, Japan.

Yu, "The role of shape selectivity in catalytic fast pyrolysis of lignin with zeolite catalysts", Applied Catalysis A: General 447-448 (2012) pp. 115-123, journal homepage: www.elsevier.com/locate/apcata.

Zhao, "Aqueous-phase hydrodeoxygenation of bio-derived phenols to cycloalkanes", Journal of Catalysis 280 (2011) 8-16, journal homepage: www.elsevier.com/locate/jcat, Germany.

Zhao, "Aromatics Production via Catalytic Pyrolysis of Pyrolytic Lignins from Bio-Oil", Energy Fuels 2010, 24, 5735-5740, China.

\* cited by examiner

SELECTIVE LIQUEFACTION OF LIGNIN AND BIOMASS IN A MIXTURE OF SUB- AND SUPERCRITICAL FLUIDS IN ABSENCE OR PRESENCE OF HETEROGENEOUS CATALYSTS

CROSS-REFERENCE TO RELATED APPLICATIONS

This application claims priority under 35 U.S.C. §119 to provisional application Ser. No. 62/217,558 filed Sep. 11, 2015, which is incorporated by reference in its entirety.

GRANT REFERENCE

This disclosure was made with government support under grant numbers IIA-1330840 and IIA-1330842 by the National Science Foundation. The government has certain rights in the disclosure.

BACKGROUND

I. Field of the Disclosure

The present disclosure relates generally to the liquefaction, and specifically selective liquefaction, of the biomass and biomass-derived products, such as lignin. More specifically, but not exclusively, the present disclosure relates to and provides inventive work covering the selective liquefaction of biomass and biomass products, for example lignin, in presence of a homogeneous and environmentally friendly carbon dioxide catalyst in supercritical state and heterogeneous inorganic catalyst or a mixture of heterogeneous inorganic catalysts in water at sub-critical, near-critical, or supercritical condition providing an ability to tune the selectivity and the yield of the organic phenolic compound or a specific and limited range of the organic phenolic compounds.

II. Description of the Prior Art

Lignin is one of the most abundant natural biopolymers produced from biomass and a major non-fossil and carbon-rich renewable source of aromatic compounds. Different processes for lignin or biomass degradation, gasification, or liquefaction and their conversion into high-value organic products are known. Degradation, gasification, or liquefaction of lignin and biomass using sub-critical, near-critical, and supercritical conditions are known.

WO2011/091044 discloses production of fermentable sugars and lignin from biomass using supercritical fluids. An optional addition of less than 10% of carbon dioxide (as an additive) in the pretreatment step in the range of 150-300° C. is considered. However, the selectivity approach in regard to production of one specific phenolic product or a number of specific phenolic products is not disclosed. Furthermore this patent is not related to the production of high-value phenolic products.

EP 2449060 A2 discloses a supercritical water gasification process and in particular catalytic gasification of organic matter in supercritical water in presence of metal catalysts supported on metal oxides ($Al_2O_3$, $Mn_xO_y$, MgO, $ZrO_2$, and $La_2O_3$) and broad range of alkali salts producing gaseous products in the processes of steam reforming, methanation, and hydrogenation.

An example is provided for p-cresol (4-methylphenol) producing gaseous products such as $H_2$, CO, $CH_4$ and $CO_2$. However, this patent is not related to the liquefaction of the said organic matter and the selectivity approach in regard to production of one specific phenolic product or a number of specific phenolic products is not disclosed.

U.S. Pat. No. 8,945,246 discloses an apparatus for producing liquefied fuel oil from lignocellulose biomass using specific organic solvents including paraffins, cyclic hydrocarbons, aromatic hydrocarbons, alcohols, phenols, ethers, ketones, esters and combination thereof. However, the '246 patent does not disclose a selectivity approach in regard to production of one specific phenolic product or a number of specific phenolic products.

None of the prior art techniques disclose selective synthesis of one specific phenolic product or a number of specific phenolic products that can be achieved by synergistic combination. As such, limitations in these and other non-enumerated areas have and do continue to exist with the current methods and approaches.

SUMMARY

Therefore, modifications and improvements to the prior art techniques are required to achieve selective synthesis of a specific phenolic product or a group of chemically related specific phenolic products rather than production of a broad spectrum of the phenolic products. In addition to selectivity, this approach requires the lowest possible temperature range with minimal energy requirements.

According to at least one exemplary aspect, a method for liquefacting a biomass or lignin in presence of a mixture of one or more sub-, near-, and supercritical fluids is disclosed. In at least one preferred form, the mixture is supercritical carbon dioxide. In yet another preferred form, the sub-, near-, and supercritical fluid is water and supercritical carbon dioxide for selective liquefaction of biomass or lignin. Still, another preferred step includes producing a phenolic product or group of chemically related phenolic products by liquefaction of the biomass or lignin. In another preferred form, the supercritical carbon dioxide catalyst is a green supercritical catalyst. Another preference, in at least one form, is a production process for a phenolic product or group of chemically related phenolic products does not require additional separation of the catalyst. Other aspects include selective liquefaction conditions for heating to a temperature from about 200° C. to about 350° C., a minimum pressure of 72.9 atm (7.39 Mpa) for achieving a supercritical state of a homogeneous carbon dioxide catalyst, and by batch, flow, or circulation reactors.

According to another exemplary aspect, a method for selective synthesis of phenolic products by means biomass or biomass products liquefaction is disclosed. The method includes, such steps as, selecting in favor of at least one phenolic compound or a mixture of phenolic compounds and synthesizing of the selected phenolic compounds from a liquid or biomass organic fraction. In another step, production of the liquid or biomass organic fraction occurs in presence of a homogeneous catalyst in supercritical state. Also, production can include a mixture of said homogeneous and one or more heterogeneous catalysts mixed with water in sub-critical, near-critical, or supercritical condition.

The present disclosure is directed to providing a process for treatment of biomass material by hydrothermal liquefaction in presence of supercritical carbon dioxide and water at subcritical, near-critical, or supercritical conditions to provide selectivity in synthesis of specific organic phenolic products or a group of chemically related specific phenolic products.

The disclosure also contemplates, amongst other applications, a method for treatment of biomass and/or lignin wherein the biomass and/or lignin are subjected to liquefaction by treatment with water at subcritical, nearcritical, or supercritical conditions achieved by pressurizing the pressure vessel with liquid or gaseous carbon dioxide and reaching a supercritical carbon dioxide fluid state in the pressure vessel.

According to one aspect, the method comprises a step when the biomass and/or lignin subjected to liquefaction by treatment with water at subcritical, near-critical, or supercritical conditions achieved by pressurizing the water with carbon dioxide reaching a supercritical carbon dioxide state, is subjected to fast heating in the beginning of the process to prevent re-polymerization of the products.

According to another aspect, the method includes a step when the biomass and/or lignin subjected to a said liquefaction by treatment with water at subcritical, nearcritical, or supercritical conditions in presence of the said supercritical carbon dioxide, is subjected to fast cooling at the end of the process to prevent the re-polymerization of the products.

According to at least one other aspect, the amount of biomass and/or lignin subjected to liquefaction by treatment with water at subcritical, near-critical, or supercritical conditions and supercritical carbon dioxide, can vary in relation to water allowing higher concentration of supercritical carbon dioxide within the pressure vessel and causing the selectivity change.

According to still another aspect, the amount of water at subcritical, near-critical, or supercritical conditions can vary in relation to the amount of biomass and/or lignin subjected to liquefaction and carbon dioxide supercritical fluid causing the selectivity change.

According to yet another aspect, the amount of supercritical carbon dioxide can vary in relation to the amount of biomass and/or lignin subjected to liquefaction and water at subcritical, near-critical, or supercritical conditions causing the causing the selectivity change.

According to still another aspect, the produced liquefied samples do not require separation of the catalyst after the end of the process of biomass/lignin liquefaction.

These and other applications leveraging the methods of the present disclosure are contemplated.

BRIEF DESCRIPTION OF THE DRAWINGS

Illustrated embodiments of the disclosure are described in detail below with reference to the attached drawing figures, which are incorporated by reference herein, and where.

BRIEF DESCRIPTION OF THE TABLES

Figure 1:
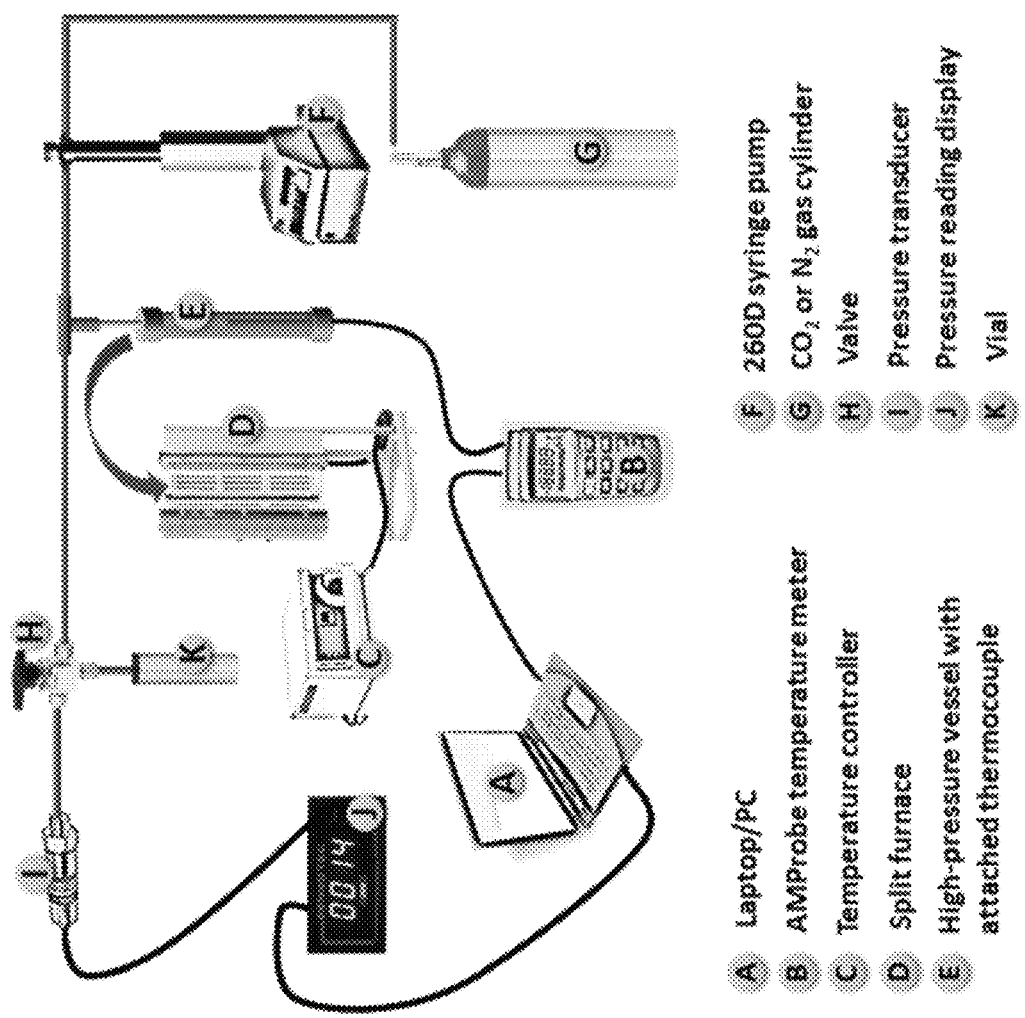
FIG. 1 is a pictorial representation a block diagram for an experimental set-up for the lignin selective liquefaction in a mixture of supercritical carbon dioxide and subcritical water fluids in accordance with an illustrative aspect of the present disclosure.

Illustrated embodiments of the disclosure are described in detail below with reference to the attached Tables, which are incorporated by reference herein, and where:

Table 1: Tentatively identified lignin-related derivatives from GC-MS (NIST11) library; and Table 2. Standards used for quantification of guaiacol derivatives.

DETAILED DESCRIPTION 1.0 Introduction

Lignin is one of the most abundant natural biopolymers and a major non-fossil and carbon-rich renewable source of aromatic compounds. In lignin, three main monomers (e.g., 4-hydroxycinnamyl alcohol, coniferyl alcohol, and sinapyl alcohol) are linked by C—O and C—C bonds forming aryl-ether β-O-4 linkages (≤50% of all lignin linkages) [i] that are responsible for a highly branched aromatic heteropolymer structure [ii]. As a result, lignin is considered one of the most promising raw materials for synthesis of high value organic products (e.g., vanillin, guaiacol, phenol, cresol, etc.) that are applicable for production of renewable polymers by ring-opening polymerization [iii], polycondensation [iv], or electrophilic aromatic substitution [v]. However, the selectivity in formation of specific phenolic products has not been fully investigated, especially in the case of alkali/kraft lignin.

In the past, various degradation processes of lignin and biomass have been studied, such as enzymatic degradation, pyrolysis, oxidation, and hydrothermal liquefaction resulting in production of aromatic aldehydes and phenolics [vi]. In case of lignin oxidative treatment, various aldehydes, e.g., syringaldehyde and vanillin as well as substituted benzoic acids have been produced [vii]. Hydrogenolysis in presence of basic [viii] catalysts (e.g., NaOH with Ru/C) and metal catalysts [ix] can be employed to cleave β-O-4 ether bonds leading to lignin liquefaction (92.5% lignin can be converted yielding 12.69% of phenolic monomers, 6.12% of aliphatic alcohols and less than 14.03% of a residual solid) based on gravimetric analyses.

To increase the amount of lower molecular weight phenolic products, lignin decomposition can be carried out in scH$_2$O (400° C.) with addition of phenol [x]. This approach resulted in a lower amount of insoluble products (23 wt. % without phenol vs. 17wt. % with phenol) and a shift toward the lower molecular weight products (from M.W.≈1500 to M.W.≤200). At a constant water density, the molecular weight of insoluble tetrahydrofuran products is lower in presence of phenol than without phenol. However, the amount of lower molecular weight phenolic products decreased at higher water densities. The conclusion can be made that the occurrence of water in the reaction medium is insignificant and only the addition of phenol caused the formation of lower molecular weight phenolic products by reacting only with the active sites pertinent to lignin depolymerization instead of other reactive sites responsible for the formation of heavier fragments [10]. Similar to lignin, biomass liquefaction in sub- and supercritical water resulted in a maximum yield of heavy oils of 53.3% at 380° C. [xi,xii]. The biomass treated in sub- and supercritical (300-400° C.) water [xiii] produced more carbon in both solid and liquid phases at higher temperatures. An increased concentration of cyclopentenones (C$_5$H$_8$O—3% to 7%) and phenols (C$_6$H$_6$O—9% to 14%) and decreased guaiacol content (C$_7$H$_8$O$_2$—28% to 20%) are explained by hydrolysis of ether bonds and alkylation of aromatic rings of the intermediate products. A hydrothermal treatment of lignin in presence of small amounts (14 wt %) of formic acid as a hydrogen donor in scCO$_2$/acetone/water fluid at 300° C. and 100 bar pressure [xiv]. However, only 12% of the aromatic compounds produced by this method.

In most of the above mentioned and other approaches the selectivity toward formation of specific phenolic products in supercritical fluids has not been highlighted. However, it can be assumed that kinetics could be a dominating factor towards selective synthesis of high-value organic products. As emphasized earlier [xv], due to fast kinetics in scH$_2$O the total carbon content in the liquid phase reaches its maximum at short residence times (~1 sec) causing the scission of lignin linkages and producing monomeric products including phenol. In subcritical water [xvi] the maximum yield of monomers can be observed at a residence time of only 2-4 seconds. These results are explained by longer time required for re-polymerization and either kinetic or quasi-thermodynamic mechanisms rather than a full thermodynamic control. Thus, treatments aiming to shift the balance of depolymerization and re-polymerization processes should be conducted at low temperatures, short residence times, and in presence of catalysts.

Therefore an objective of the present disclosure is to validate the hypothesis that the presence of carbon dioxide as a second component in a near critical mixture with water can significantly increase the phenolic yield and selectivity toward formation of specific high-value phenolic products. To achieve this objective, the results obtained for a H$_2$O—CO$_2$ system at sub- and supercritical conditions at varied temperatures are compared with a baseline system containing H$_2$O pressurized by an inert gas (N$_2$). The liquid and solid phase products are characterized using liquid-liquid extraction (LLE) with GC-MS and pyr-GC-MS, respectively. In the present disclosure, a novel thermal carbon analysis (TCA) method yielding a carbon mass balance closure is disclosed. Objects achieved include, at least, a systematic analysis of the temperature effect on lignin decomposition in a mixture of sub- and supercritical environmentally benign solvents.

2.0 Exemplary Materials & Methods 2.1. Materials

Alkali lignin and 4-chloroacetophenone is commercially available for purchase from Sigma Aldrich. Deionized water can be obtained using a Milli-Q® Integral Water Purification System (EMD Millipore Corp. Billerica, Mass., USA). For liquid-liquid extraction, acetic acid and dichloromethane (DCM) of GC quality can be obtained from Sigma Aldrich (Atlanta, Ga., USA). The reactor, tubing and fittings are commercially available for purchase from High Pressure Equipment Company (Erie, Pa., USA) and Swagelok (Solon, Ohio, USA).

2.2. Sub- and Supercritical Hydrothermal Treatment of Lignin

The hydrothermal treatment of alkali lignin at sub- and supercritical conditions in a temperature range of 200-500° C. can be carried out in a stainless steel high-pressure vessel (316 SS) having a capacity of 12 mL with a pressure tolerance of up to 103 MPa. A type K thermocouple can be inserted through the bottom of the vessel to measure the temperature inside the vessel by an AMProbe temperature meter. The internal pressure can be controlled by the pressure sensor connected to the monitor. To achieve reproducible synthesis conditions for each sample, the temperature ramp can be adjusted in each experiment. A complete set-up for the hydrothermal procedure is shown in a block diagram (FIG. 1).

In each experiment, 0.1 g of lignin can be placed inside the vessel and 6 mL of deionized water can be added to disperse the lignin. The vessel with the inserted thermocouple can be sealed and placed into the split Carbolyte furnace for hydrothermal treatment. In order to reach the targeted temperature within the shortest period of time, the initial set-up temperature of the Carbolyte temperature controller can be adjusted to 650° C. with a ramp rate of 100° C./min. Depending on the synthesis conditions, after 2-5 min the temperature can be adjusted to the required value. The pressure inside the vessel (22.063 MPa) can be maintained by a Teledyne syringe pump 260D pre-pressurized with $CO_2$ or $N_2$. When the pressure and temperature requirements are met, a stopwatch can be used to record the residence time. During this time period, the temperature and pressure inside the vessel can be continuously monitored. After 10 minutes, the furnace can be turned off and the pressure released. The reaction can be then quenched by the immersion of the reaction vessel into cold water.

The liquid that came out through the pressure valve during the pressure release can be collected and combined with the liquid phase collected from the reactor to measure the final weight. The collected liquid phase can be characterized using TCA, LLE with GC-MS and total organic carbon (TOC). The solid phase can be collected from the vessel after an overnight drying, weighed and characterized using pyr-GC-MS.

2.3. Characterization of Liquid Phase Products

Figure 2:
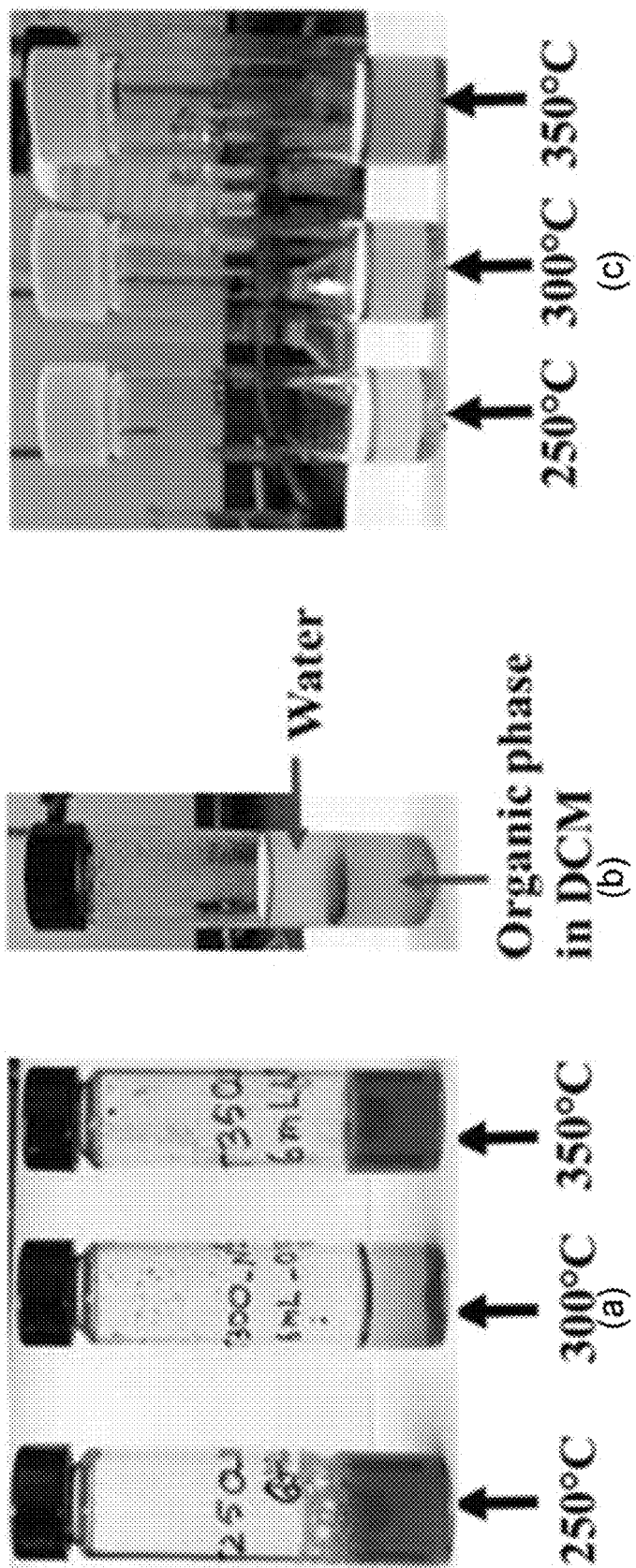
FIG. 2 is a set of images of a water-organic phase mixture after selective liquefaction of 0.1 g lignin in presence of 6 mL of water before liquid-liquid extraction (left), separated water-organic phase layers after addition of dichloromethane (center), and organic phases produced at three different temperatures separated from the aqueous phase after liquid-liquid extraction (right) in accordance with an illustrative aspect of the present disclosure.

After hydrothermal treatment, the liquid phase can be characterized using LLE with GS-MS, TOC and TCA. The liquid bio-oil phase collected after the hydrothermal sub- or supercritical treatment can be separated from the aqueous phase by a LLE using DCM and weighed upon drying. In a first step of extraction, 10 μL of acetic acid can be added to every 1 mL of a liquid sample while adjusting pH to ~4.0. Then the recovery standard (4-chloro-acetophenone) can be added enabling monitoring and correction for losses during extraction. The sample (FIG. 2(a)) can then be extracted three times with 1 mL of DCM with vigorous shaking. After the DCM (bottom layer) and the water (top layer) phases separated completely (FIG. 2b), the bottom layers can be collected and combined (FIG. 2(c)), and then the internal standard can be added. The quantification can be based on the response factors of individual standards. If the corresponding standards are not available, structurally similar compounds can be used (details are provided in Supplementary Information Table 1).

TABLE 1

Tentatively identified lignin-related derivatives from GC-MS (NIST11) library.

| Name of the compound* | IUPAC name | RT** | m/z | Quantification ion |
|---|---|---|---|---|
| O-Cresol | 2-methyl phenol | 8.26 | 108 | $C_7H_8O$ |
| p-Cresol | 4-methylphenol | 8.65 | 108 | $C_7H_8O$ |
| Benzene,1,2dimethoxy- | 1,2-dimethoxybenzene | 9.71 | 138 | $C_8H_{10}O_2$ |
| Phenol, 3,5-dimethyl- | 3,5dimethylphenol | 9.77 | 122 | $C_8H_{10}O$ |
| Phenol, 3-ethyl- | 3-ethylphenol | 10.04 | 122 | $C_8H_{10}O$ |
| Creosol | 2-methoxy-4-methylphenol | 10.28 | 138 | $C_8H_{10}O_2$ |
| Phenol, 3-ethoxy- | 3-ethylphenol | 10.42 | 138 | $C_8H_{10}O_2$ |
| m-Guaiacol | 2-methoxyphenol | 10.92 | 124 | $C_7H_8O_2$ |
| 2,3-Dimethoxytoluene | 1,2-dimethoxy-3-methylbenzene | 11.11 | 152 | $C_9H_{12}O_2$ |
| 1,2-Benzenediol,3 methyl- | 3-methylbenzene-1,2-diol | 11.40 | 124 | $C_7H_8O_2$ |
| Phenol,4-ethyl-2 methoxy- | 4-ethyl-2-methoxyphenol | 11.49 | 152 | $C_9H_{12}O_2$ |
| Phenol,4-(aminomethyl)-2-methoxy | 4-(aminomethyl)-2-methoxyphenol | 11.75 | 153 | $C_8H_{11}NO_2$ |
| 2-Ethoxy-4-methylphenol | 2-ethoxy-4-methylphenol | 11.81 | 152 | $C_9H_{12}O_2$ |
| Benzene,4-ethyl-1,2 dimethoxy- | 4-ethyl-1,2-dimethoxybenzene | 12.30 | 166 | $C_{10}H_{14}O_2$ |
| Phenol, 2,6-dimethoxy- | 2,6 dimethoxyphenol | 12.71 | 154 | $C_8H_{10}O_3$ |
| Eugenol | 2-methoxy-4-prop-2-enylphenol | 12.82 | 164 | $C_{10}H_{12}O_2$ |
| 4-Ethylcatechol | 4-ethylbenzene-1,2-diol | 13.12 | 138 | $C_8H_{10}O_2$ |
| Vanillin | 4-hydroxy-3-methoxy benzaldehyde | 13.43 | 152 | $C_8H_8O_3$ |
| trans-Isoeugenol | 2-methoxy-4-[(1E)-1-propen-1-yl] phenol | 13.52 | 164 | $C_{10}H_{12}O_2$ |
| Phenol, 2-butyl- | 2-butylphenol | 14.02 | 150 | $C_{10}H_{14}O$ |
| Phenol,2-methoxy-4 propyl | 2-methoxy-4-propylphenol | 14.16 | 166 | $C_{10}H_{14}O_2$ |
| 1,3-Benzenediol,4propyl- | 4-propylbenzene-1,3-diol | 14.35 | 152 | $C_9H_{12}O_2$ |
| 1,2-Dimethoxy-4-n-propylbenzene | 1,2-dimethoxy-4 propylbenzene | 14.78 | 180 | $C_{11}H_{16}O_2$ |
| 2-Propanone,1-(4-hydroxy-3-methoxyphenyl)- | 1-(4-hydroxy-3-methoxyphenyl)propan-2-one | 15.08 | 180 | $C_{10}H_{12}O_3$ |
| Benzene,4-butyl-1,2-dimethoxy- | 4-butyl-1,2-dimethoxybenzene | 15.28 | 194 | $C_{12}H_{18}O_2$ |
| Methyl-(2-hydroxy-3-ethoxy-benzyl)ether | 2-ethoxy-6-(methoxymethyl) phenol | 16.51 | 180 | $C_{10}H_{12}O_3$ |

*The names of compounds are based on the identification using MS NIST library;
**Retention time The relative yield obtained for LLE GC-MS analysis is defined as:

$$\text{Relative yield} = \frac{\text{Area under the peak}}{\text{Total area of the peaks}} 100\%$$

The GC-MS analyses can be performed using a commercially available Agilent 5890N GC equipped with 5971 MSD (EI). All injections (1.0 μL) can be conducted in a splitless mode (0.5 min) for 1.0 min using a splitless liner with deactivated glass wool (Restek, Bellefonte, Pa.). A 50 m DB-5MS column (J&W Scientific, Inc., Folsom, Calif., USA) with a 0.25 mm I.D. and a 0.25 μm film thickness can be used for all separations. Ultra-pure helium (99.999%) can be used as a carrier gas with a constant flow rate of 1.0 mL min-1. The initial oven temperature are set to 40° C. held for 1.0 min, then ramped to 140° C. with a rate of 20° C./min, then ramped to 290° C. with a rate of 10° C., and held for 12 min. The injector and transfer line temperatures can be set at 250 and 280° C., respectively. All MS data can be acquired in total ion current (TIC) mode with a mass range of 50-550 m/z. The total organic carbon analyzer employed was Sievers InnovOx laboratory TOC analyzer with a GE autosampler. For TOC analysis, the liquid phases obtained after the hydrothermal treatment at 200, 300 and 400° C. is filtered, centrifuged at 13,000 rpm for 10 min to remove the particles, and diluted with distilled water to 33% by volume. Distilled water (17.8 MΩ·cm at 25° C.) can be used as a TOC blank.

The TCA can be performed on a thermal optical analyzer commercially available for purchase from Sunset Laboratories Inc. (Tigard, Oreg., USA). At least one advantage of the TCA instrument is that it enables desorption and pyrolysis of the carbonaceous species at temperatures from 200-850° C. under inert (helium). Then, after all volatile species evolved, the heating is conducted under oxidation atmosphere (in presence of oxygen) to quantitatively generate $CO_2$, which is converted to methane and quantified using flame ionization detection calibrated with methane. The use of this method ensures the comprehensive determination of all of the carbon in a sample.

2.4. Characterization of Solid Phase Products

Due to the small size of the supercritical vessel and the initial sample mass, the weight of the solid phase product is estimated as nearly 50% for high temperature hydrotreatment. This value provides an approximate evaluation of the depolymerization process. The solid phase left over after the near critical hydrothermal treatment of lignin can be characterized using a pyrolyzer GCMS (pyr-GC-MS) Shimadzu QP2010 Ultra equipped with an automatic sampler commercially available for purchase from Frontier with the injection port temperature set at 250° C. and the furnace operating at 500° C. For each sample, approximately 100 μg of a solid phase sample are weighed and placed in a sample holder provided by Frontier. For identification of the solid-state products, the NIST mass spectral library with a search program (version NIST 14) can be used.

3.0 Results and Discussion

Two near critical fluid mixtures, specifically $H_2O$—$CO_2$ and $H_2O$—$N_2$, can be chosen for the hydrothermal degradation of lignin. In those mixtures, one of the components (water) is present at a constant concentration defined by the volume of water in the supercritical vessel (6 mL). The second component (carbon dioxide) can be used for pressurization. To identify the specific effects of carbon dioxide, the results can be repeated with $N_2$ as an inert gas.

At 22.063 MPa in an experimental temperature range of 200-500° C., both nitrogen and carbon dioxide occur as supercritical fluids, however water becomes supercritical only at 374° C. whereas in the lower temperature range (250-350° C.) it is present in a subcritical phase. Complex interactions between two fluids under near critical conditions and the properties of carbon dioxide in near critical water affect the mutual solubility of the reagents [xvii], chemical reactions, and kinetics of the catalytic processes that take place on the surface of lignin. Furthermore, the gaseous and phenolic species produced during hydrothermal treatment are known to catalyze lignin depolymerization [10], which makes the analysis of lignin depolymerization even more complicated.

The gravimetric analysis showed that 40-50% of lignin are converted into bio-oil (organic extractable products) in a temperature range of 300-500° C., the rest being a solid phase product. The amount of gases released during the process has not been measured, however, as the mass balance can be closed without taking it into account, the mass of the gases appears to be negligible in comparison to other phases.

3.1 LLE-GC-MS Analysis of the Liquid Organic Phases.

Figure 3:
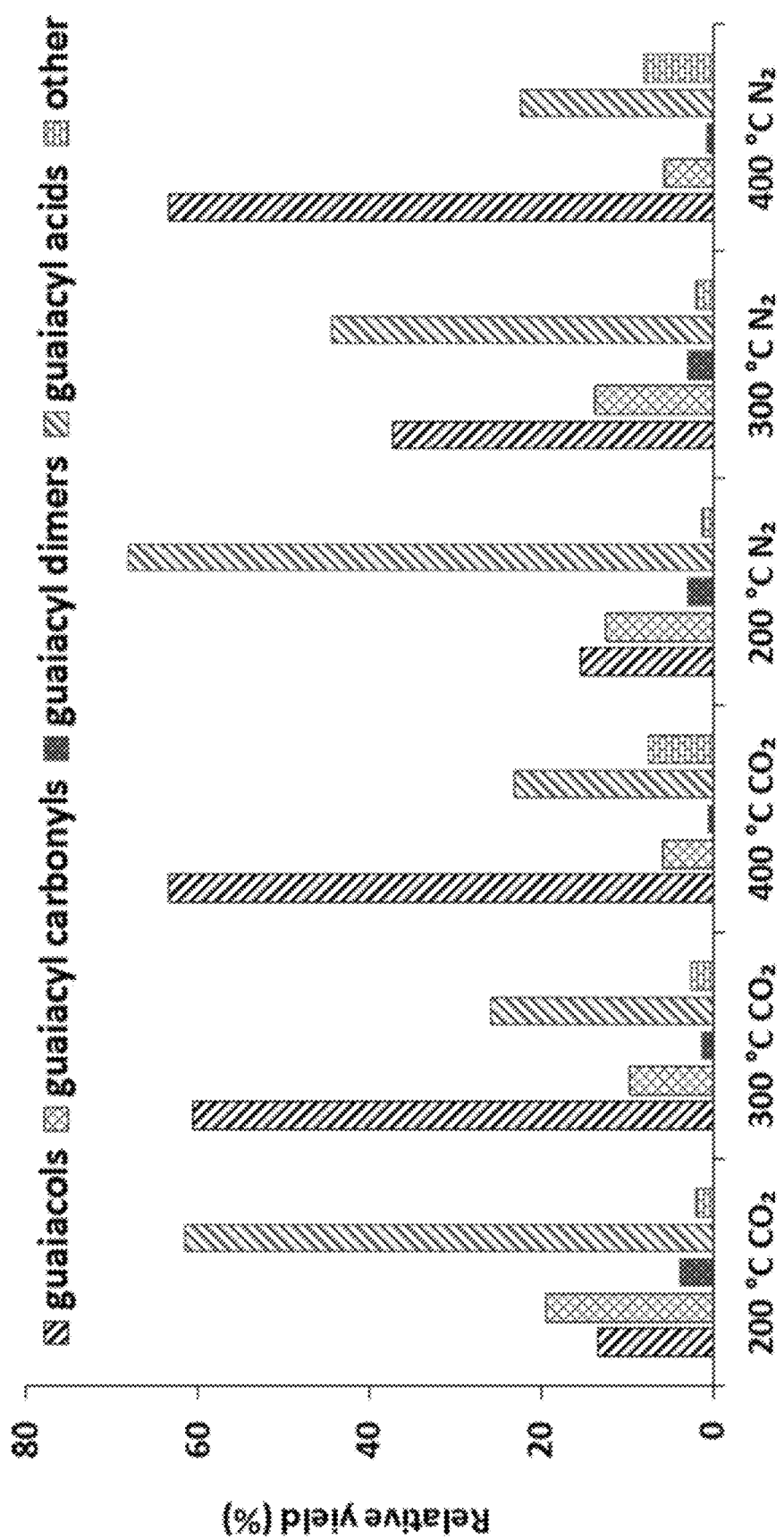
FIG. 3 is a pictorial representation of GC-MS analysis data of the phenolic products formed after lignin hydrothermal treatment at different temperatures and constant pressure (22.063 MPa) in the presence of water-carbon dioxide or water-nitrogen sub- and supercritical fluids in accordance with an illustrative aspect of the present disclosure.

The comparative GC-MS results for the lignin decomposition products formed in $H_2O$—$CO_2$ and $H_2O$—$N_2$ near critical fluid mixtures within a temperature range of 300-400° C., constant pressure (3200 psi), fixed residence time (10 min), and the experimental yield equal to or greater than 5% are presented in FIG. 3. Focusing mainly on selective production of specific phenolic compounds in a mixture of sub- and supercritical fluids from alkali lignin, FIG. 3 shows only representative classes of compounds that are produced.

The lignin degradation started at lower temperatures (e.g., 200° C.), but the guaiacol derivatives as main phenolic products is observed only at higher temperatures for both $H_2O$—$N_2$ and $H_2OCO_2$ near critical mixtures, which is in good correlation with the previously published results [2]. As a general trend, guaiacyl acids represented primarily by homovanillic acid are the main products at lower temperature treatments but their amounts declined in samples obtained at higher temperatures being replaced with guaiacol derivatives, i.e., guaiacol itself and its methyl, ethyl and propyl homologs (FIG. 3; for a detailed list, see Supplementary Table 1). A similar trend can also be observed for quaiacyl carbonyls (represented mainly by vanillin) and quaiacyl dimers tentatively identified based on mass spectra similar to quaiacol and molecular ions of 372 and 372 amu.

The most significant difference between the $CO_2$- and $N_2$-treated samples is observed at 300° C. Namely, guaiacols are recovered in higher abundance (FIG. 3) as the main products in presence of $CO_2$, with relative yields of 60% in contrast to merely 37% in presence of $N_2$. Guaiacyl acids are the second most abundant group of products. By contrast, guaiacyl acids are the main products when the process is conducted at 300° C. in presence of $N_2$. When the treatment temperature is increased to 400° C., the difference between the $CO_2$- and $N_2$-treated samples is no longer observed.

The observed difference between $H_2O$—$CO_2$ and $H_2O$—$N_2$ at 300° C. with respect to a higher selectivity in formation of guaiacols can be explained by the presence of carbon dioxide as an acidic homogeneous catalyst that affects the pathways of lignin depolymerization [xviii]. The catalyst-enabled selectivity is expected to diminish at higher temperatures just as observed. The striking difference between the 300 and 400° C. $CO_2$-treated samples may partially be due to the decrease in solubility of $CO_2$ in water from 2.9 mol % at 300° C. to 2.0 mol % at 400° C. under ~22.0 MPa) [17].

Select experiments can be conducted at 500° C. in the $H_2O$—$N_2$ system and their results corroborated these conclusions. As expected, guaiacol is detected at the highest yield, as high as 75% at 500° C. However, also as expected for high temperature processes, other phenolic derivatives are observed such as phenol and its homologs signifying lower selectivity.

3.2 Total Organic Carbon Analysis

Figure 4:
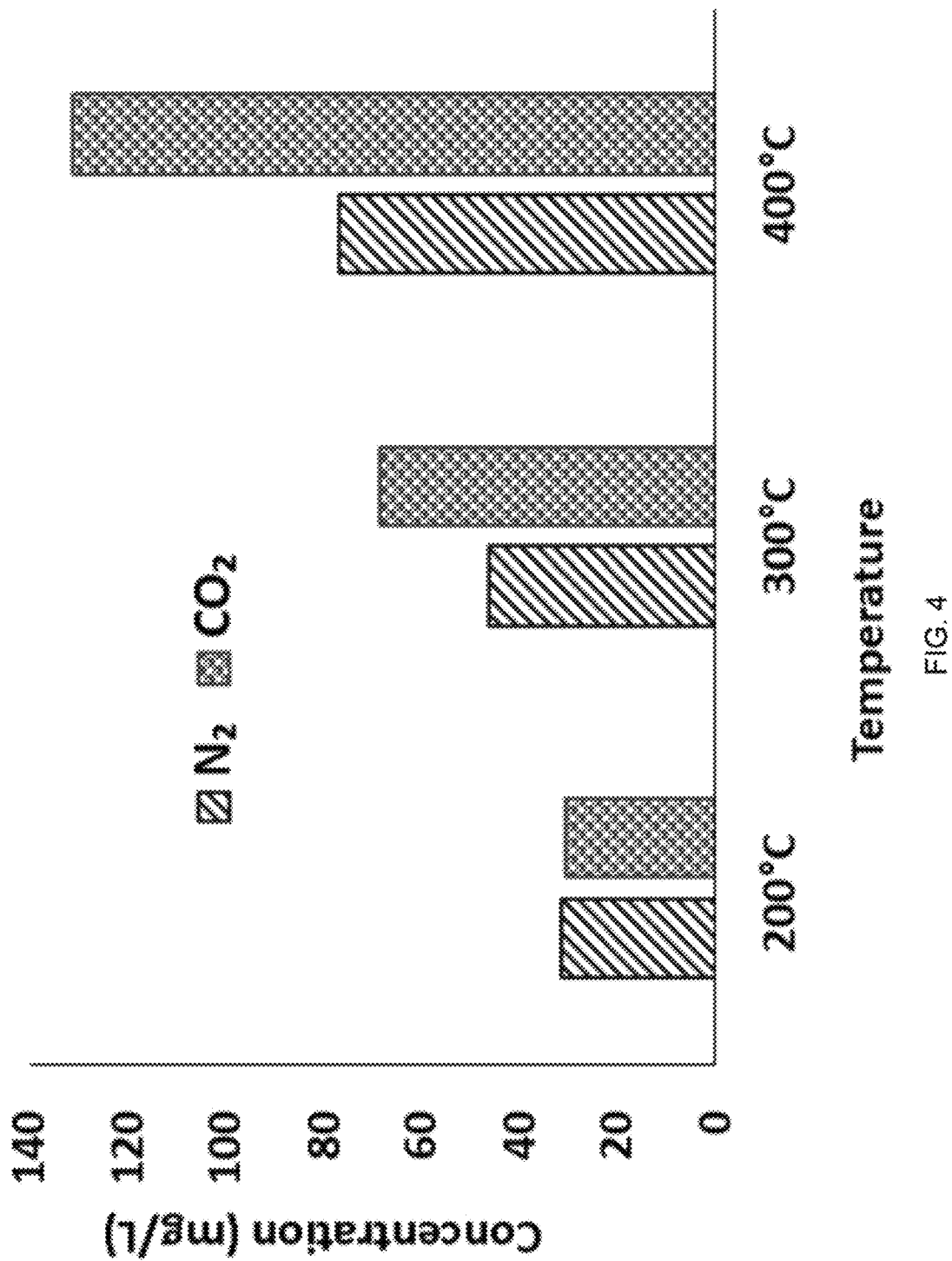
FIG. 4 is a pictorial representation of concentrations of the total organic carbon (TOC) for different hydrotreatment temperatures in $H_2O$—$CO_2$ and $H_2O$—$N_2$ systems in accordance with an illustrative aspect of the present disclosure.

The results of the TOC evaluation for $H_2O$—$CO_2$ in comparison to $H_2O$—$N_2$ near critical fluids at 200, 300 and 400° C. are presented in FIG. 4. At 200° C., the total carbon content is higher in the $H_2O$—$N_2$ system than in the $H_2O$—$CO_2$ system. By contrast, the amount of carbon becomes higher in $H_2O$—$CO_2$ than in $H_2O$—$N_2$ at 300° C. Yet after further increasing the temperature of the hydrothermal treatment to 400° C., the total amount of carbon again becomes higher in the $H_2O$—$N_2$ system than with $CO_2$. These observations corroborate the GC results and also provide a new information about the process, as TOC allows for a comparison of the total carbon in the liquid phase for varied process conditions. The TOC decrease in the water-$CO_2$ system when the treatment temperature is increased from 300 to 400° C., in contrast to a similar temperature change without $CO_2$, is consistent with the conclusion of catalysis by carbon dioxide leading to a greater guaiacol production.

3.3 Thermal Carbon Analysis of the Liquid Phase Products

Figure 5:
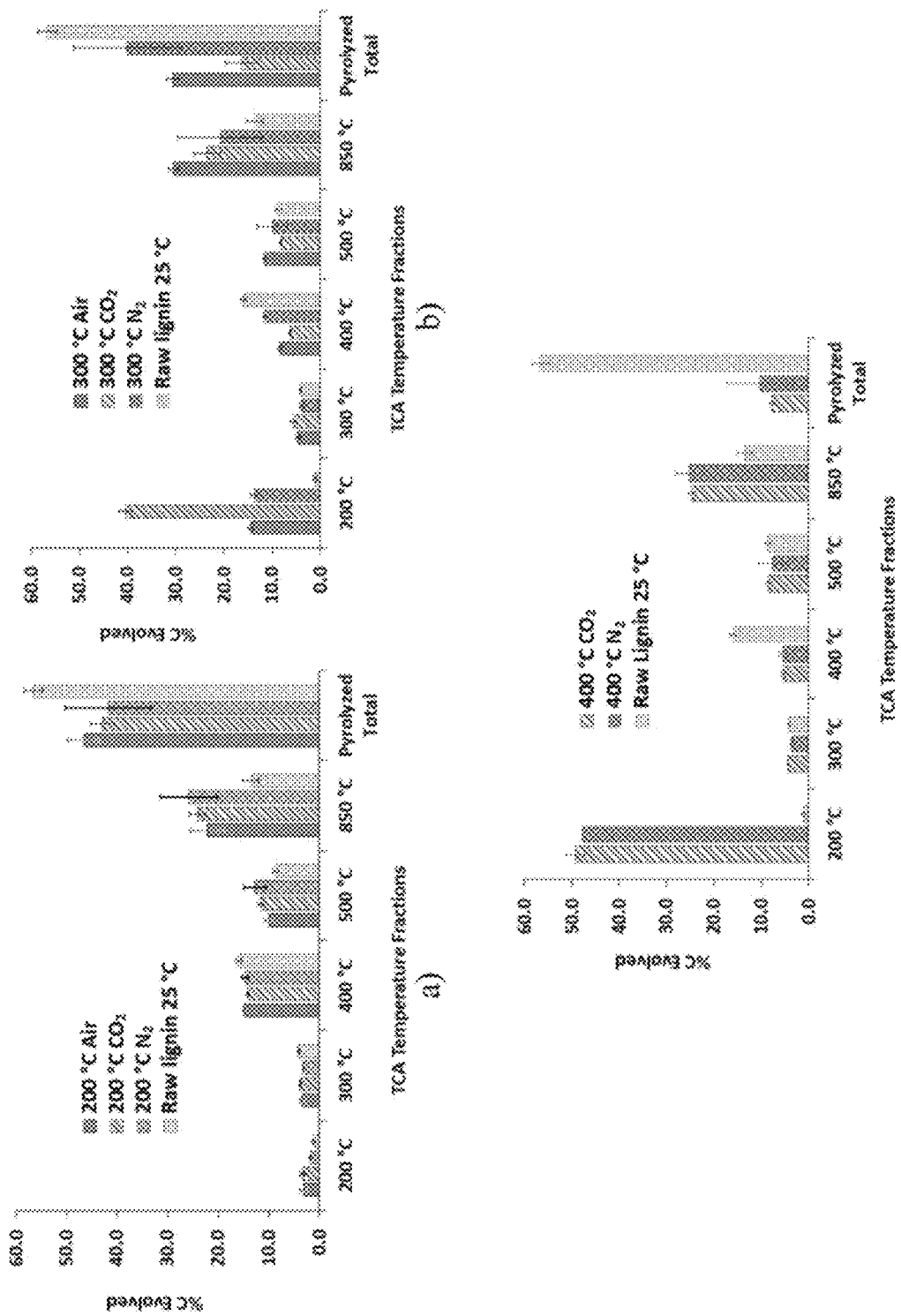
FIG. 5 is a pictorial representation of Thermal Carbon Analysis (TCA) of the liquid organic phase produced from lignin decomposition in $H_2O$—$CO_2$ and $H_2O$—$N_2$ near critical fluids at: (a) 200° C.; (b) 300° C., and (c) 400° C. in accordance with an illustrative aspect of the present disclosure.

The comparative results of the thermal carbon analysis of the liquid mixed organic/aqueous phase produced in $H_2O$—$CO_2$ or $H_2O$—$N_2$ near critical fluids at 200, 300 and 400° C. are presented in FIG. 5 in panels a, b and c, respectively.

The benefit of TCA is in obtaining a comprehensive distribution of carbonaceous species in the entire liquid sample, for both the untreated (raw) lignin and products of its decomposition obtained as a result of hydrotreatment, thus allowing for their comparison. The temperature fractions reported from TCA can be differentiated as those desorbing small molecular weight compounds (200, 300° C.), pyrolyzed large molecular weight compounds (400-850° C.) and the final fraction evolving in presence of oxygen only after all volatiles vaporized at high temperature. This last fraction represents recalcitrant pyrolyzed carbon (char) formed during the TCA heating process. It is of note that raw undegraded lignin shows as much as 60 wt % in this recalcitrant "char" fraction. For the lignin samples produced in $H_2O$—$CO_2$ or $H_2O$—$N_2$ near critical fluids at 200° C., no difference is detected including an abundant pyrolyzed carbon fraction (FIG. 5($a$)) meaning that this temperature is not sufficient for lignin depolymerization. By contrast, the TCA profiles of lignin samples produced by the thermal lignin treatment in $H_2O$—$CO_2$ or $H_2O$—$N_2$ near critical fluids at 300° C. show a major difference compared to TCA of the raw lignin (FIG. 5($b$)). Apparently, as a result of such a high temperature treatment, most of the lignin is converted into volatilizable products to provide the highest observed organic carbon content at the expense of "char" carbon. The catalytic effect of $CO_2$ for the treatment at 300° C. shows as the difference in the amounts of carbon evolving at 200° C. with and without $CO_2$ (FIG. 5($b$)) corroborating the GC data. A significantly higher concentration of pyrolyzed carbon (41%) is observed in the samples treated at the same temperature in $N_2$-water in comparison to the samples produced in the $CO_2$-water system (16%).

At 400° C. (FIG. 5($c$)), the highest amount of carbon evolving at 200° C. is detected, as expected, also corroborating the above-discussed GC data. Concurrently with volatile monomer accumulation, the char carbon fraction further declined compared to lower hydrotreatment temperatures. In contrast to the hydrotreatments at 300° C., no difference between the $H_2O$—$CO_2$ or $H_2O$—$N_2$ systems is observed for the 400° C. treatments indicating that the process at this high temperature does not require $CO_2$ as a catalyst.

As a result of the thermal carbon analysis in the produced liquid phase in a temperature range of 200-400° C., a conclusion can be made that lignin depolymerization is more efficient in $H_2O$—$CO_2$ than in $H_2O$—$N_2$ near critical fluids only at moderately high temperatures, e.g., 300° C. In presence of carbon dioxide, higher concentrations of the monomers are produced at this temperature in combination with lower amounts of pyrolyzed carbon.

3.4 Pyr-GC-MS Data

Figure 6:
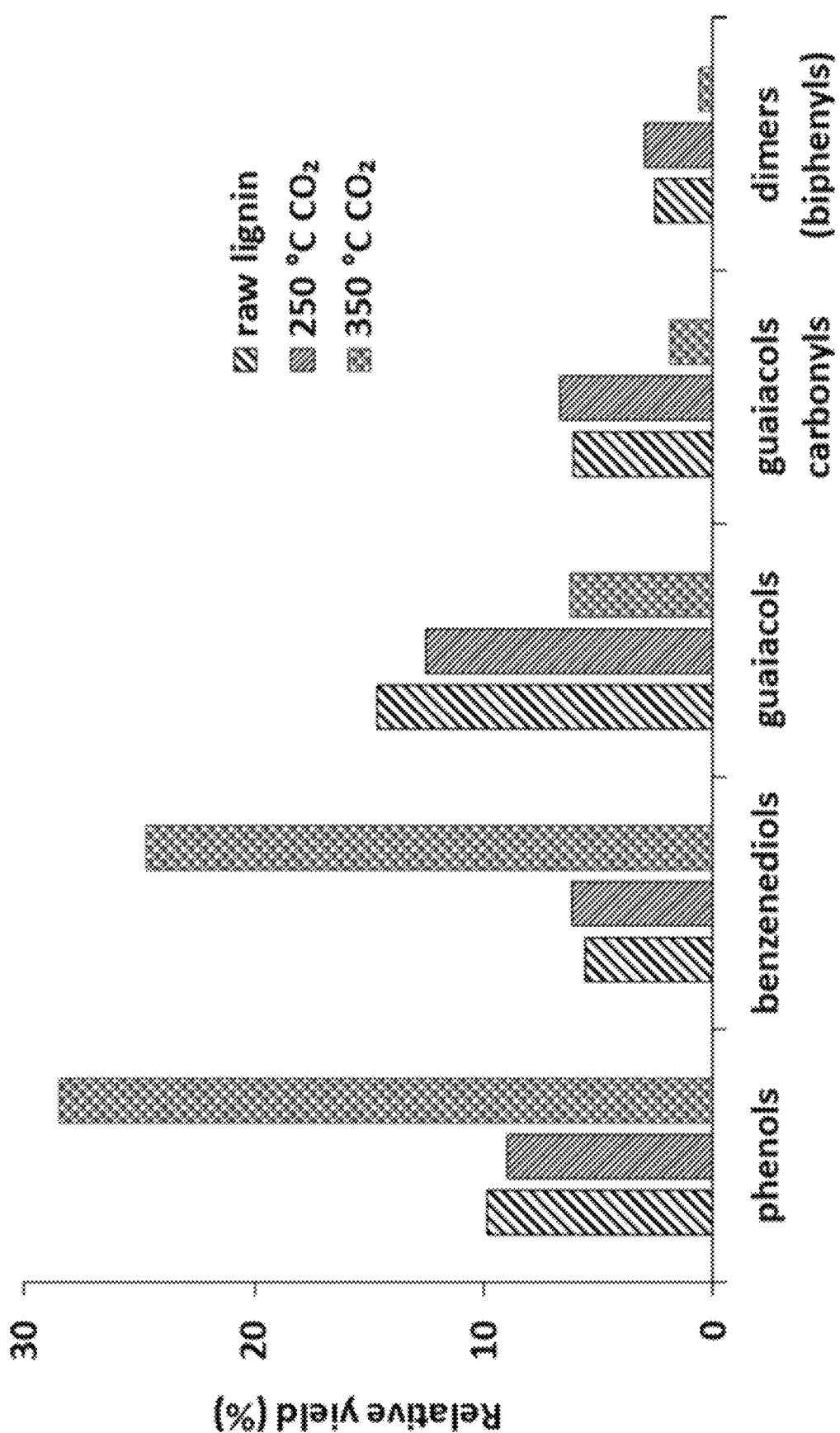
FIG. 6 is a pictorial representation of Pyr-GC-MS data for the solid phase obtained for (a) raw alkali lignin and after its exposure to the hydrothermal sub- or supercritical conditions in presence of $CO_2$ at 250 and 350° C. in accordance with an illustrative aspect of the present disclosure.

As a result of lignin depolymerization in $H_2O$—$CO_2$ or $H_2O$—$N_2$, significant amounts of solid phase products are produced yielding up to 50 wt. % of the initial lignin amount of 0.1 g. Up to 300° C. hydrotreatment, the solid phase (visually appearing only slightly darker than the raw lignin) is collected as a powder without tar or char formation. The samples hydrothermally treated at higher temperatures (400 and 500° C.) are much darker indicating a partial char formation. However, in comparison to previous reports [8], no tar is produced. The results of the pyr-GC-MS of the solid state phase produced in $H_2O$—$CO_2$ at two temperatures around the key temperature of 300° C. are presented in FIG. 6. The data shows that phenolic products make up the solid phase formed as a result of lignin depolymerization, so the solid phase product can be utilized as an additional source of valuable phenolics. However, a more detailed analysis showed that the composition of these solid phase products is similar to the original lignin only for low hydrotreatment temperatures, up to 250° C. whereas the solid phase obtained at 350° C. showed a significant increase in the content of both phenols and benzenediols at the expense of guaiacols, guaiacol carbonyls and guaiacyl dimers (FIG. 6). Representative phenolic compounds are cresol and creosol derivatives (details are provided in Table 2), whose amounts increased with the treatment temperature. Thus, the solid phase is significantly different in its monomer composition from the liquid phase monomeric products.

TABLE 2

Standards used for quantification of guaiacol derivatives.

| Compounds quantified | Standards used for quantification | GC-MS Quantification ion (M.W) |
|---|---|---|
| Phenol | Phenol | 94 |
| Guaiacol | Guaiacol | 109 |
| Methylguaiacol | Methylguaiacol | 138 |
| Ethylguaiacol | Propylguaiacol | 137 |
| Syringol | Syringol | 154 |
| Eugenol | Eugenol | 164 |
| Propylguaiacol | Propylguaiacol | 137 |
| Vanillin | Vanillin | 151 |
| Eugenol Derivative | Eugenol | 164 |
| Propenylguaiacol | Propylguaiacol | 137 |
| Propylguaiacol-Isomer | Acetovanillone | 151 |
| Acetovanillone | Propylguaiacol | 137 |
| Acetonylguaiacol | Propylguaiacol | 137 |
| Homovanillic Acid | Homovanillic Acid | 137 |
| Diguaiacyl $C_2H_4$ | Acetovanillone | 151 |
| Diguaiacyl $C_2H_2$ | Acetovanillone | 151 |

TABLE 2-continued

Standards used for quantification of guaiacol derivatives.

| Compounds quantified | Standards used for quantification | GC-MS Quantification ion (M.W) |
|---|---|---|
| Recovery standard (RS) | RS (4-chloro-acetophenone) | 139 |
| Internal standard (IS) | IS (o-terphenyl) | 230 |

3.5 A Pathway for $CO_2$ Catalyst

Despite the lower TOC yield, the use of 300° C. rather than 400° C. as a treatment temperature is a more economical option considering the energy savings. Given that the lignin treatment at this temperature appears to be efficient and also most selective only in the presence of $CO_2$, a potential explanation of its role may be as follows.

Figure 7:
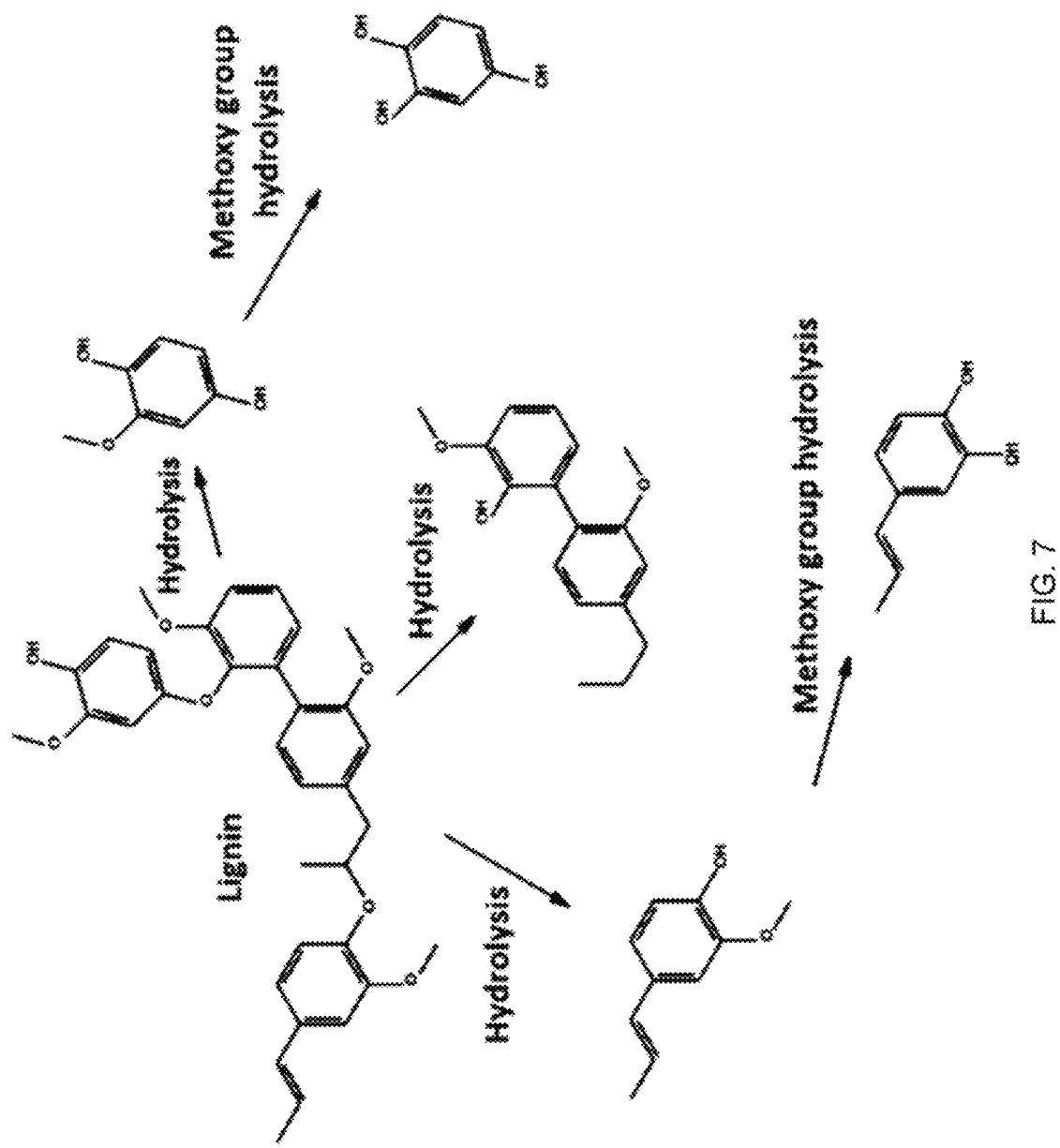
FIG. 7 is a pictorial representation of a simplified scheme of lignin degradation in accordance with an illustrative aspect of the present disclosure.

As an aromatic heteropolymer, lignin in the process of hydrothermal treatment forms various phenols and methoxy-phenols through the hydrolysis of ether β-O-4 bond [1,7]. Degradation of lignin can proceed further through hydrolysis of methoxy groups, without compromising the stability of the benzene ring itself (FIG. 7) [19].

In sub-or supercritical condition, water is a rather strong oxidant [6,xix]. However, the presence of CO2 also increases the acidity of the near critical environment potentially promoting the β-O-4 scission as a homogeneous acidic catalyst.

3.6 Exemplary Embodiments

The various embodiments disclosed herein, provide methods in selective synthesis of biomass or biomass derived products, e.g. lignin, in presence of supercritical carbon dioxide fluid in a mixture with sub-, near-, or supercritical water. In this regard, the method of the present disclosure validate that the selectivity of the biomass or biomass-related product liquefaction can be tuned by the corresponding changes in the relative amount of the sub-, near-, or supercritical water amount and supercritical carbon dioxide resulting in production of a specific phenolic product or a group of chemically related specific phenolic products.

3.6.1 Example 1

Figure 9:
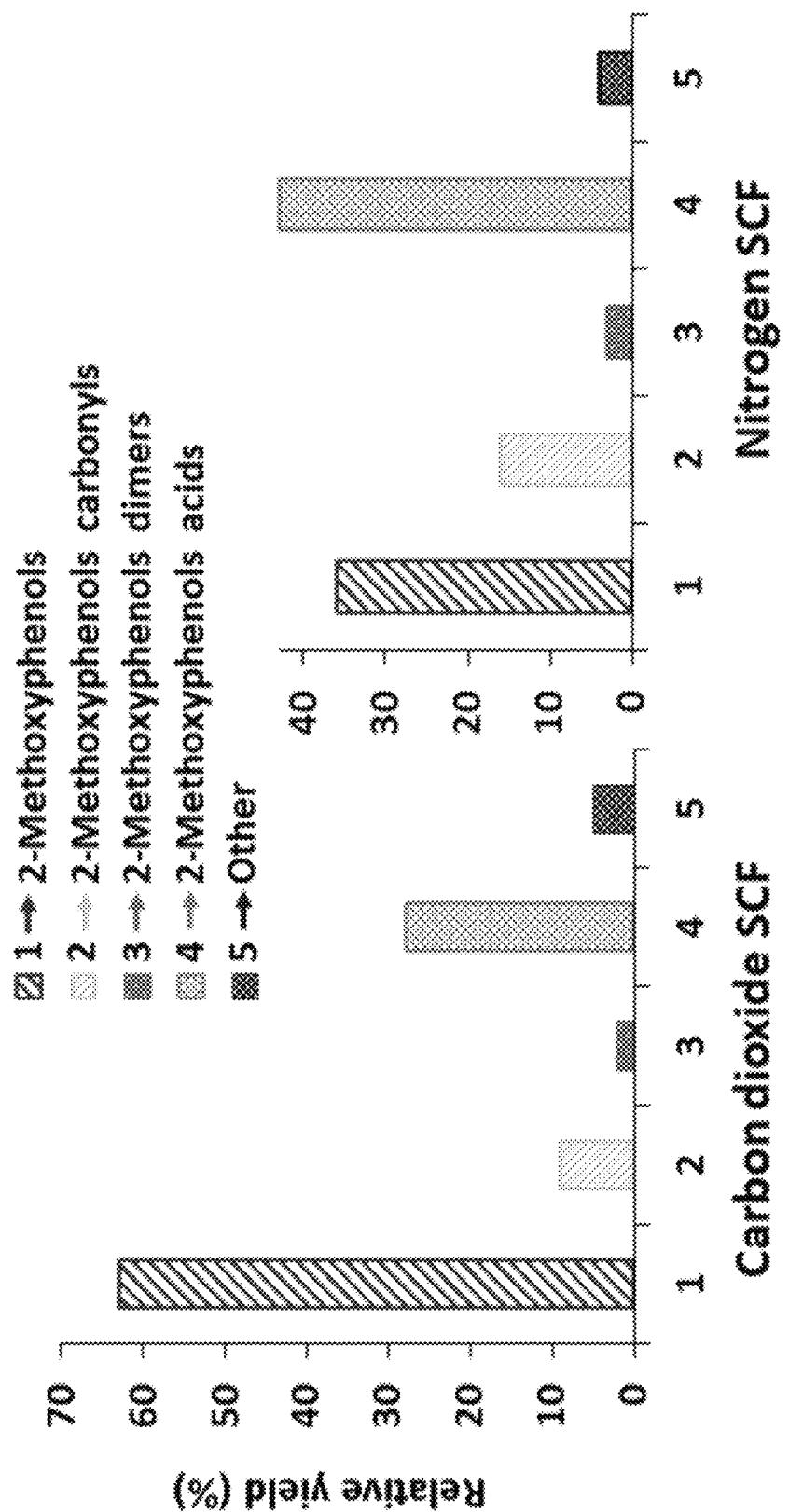
FIG. 9 is a pictorial representation of the GC-MS analysis results of the liquefied sample produced from alkali lignin in accordance with an illustrative aspect of the present disclosure.

In accordance with at least one exemplary method, 0.1 g of lignin can be placed inside the vessel and 6 mL of deionized water are added to disperse the lignin. The vessel (FIG. 1) with the inserted thermocouple can be sealed and placed into the split Carbolyte furnace for the treatment. In order to reach the targeted temperature within the shortest period of time, the initial set-up temperature of the Carbolyte temperature controller can be adjusted to 650° C. with a high ramp rate of 100° C./min. Depending on the synthesis conditions, after 2-5 min the temperature can be adjusted to the required value of 300° C. The pressure inside the vessel (22.063 MPa) can be maintained by a Teledyne syringe pump 260D pre-pressurized with $CO_2$ or $N_2$. When the pressure and the temperature requirements are met, a stopwatch can be used to record the residence time. During this time period, the temperature and the pressure inside the vessel is continuously monitored. After 10 minutes, the furnace is turned off and the pressure is released. The reaction vessel with reaction products is then quenched by the immersion of the vessel into the cold water. The results of the GC-MS analysis for the liquefied products derived from alkali lignin sample are presented in FIG. 9.

The results illustrate that in comparison to $N_2$, the carbon dioxide supercritical fluid increases the overall phenolic yield with the predominant formation of 2-methoxyphenol (guaiacol) (60%). The difference between the samples processed in presence of supercritical carbon dioxide and nitrogen at 300° C. is presented in FIG. 9. Specifically, the 2-methoxyphenols are produced with higher yield as the main products in presence of supercritical carbon dioxide, with relative yields of 60% in contrast to only 37% in presence of nitrogen. The 2-methoxyphenol-based (guaiacyl) acids are the second most abundant group of products. On contrary, the 2-methoxyphenol-based acids are the main products when the process is conducted at 300° C. in presence of $N_2$. The observed difference with respect to a higher selectivity in formation of 2-methoxyphenols can be specifically explained by the presence of carbon dioxide as an acidic homogeneous catalyst in its supercritical state that affects the pathways of selective lignin liquefaction. No tar or char formation is detected.

3.6.2 Example 2

Figure 8:
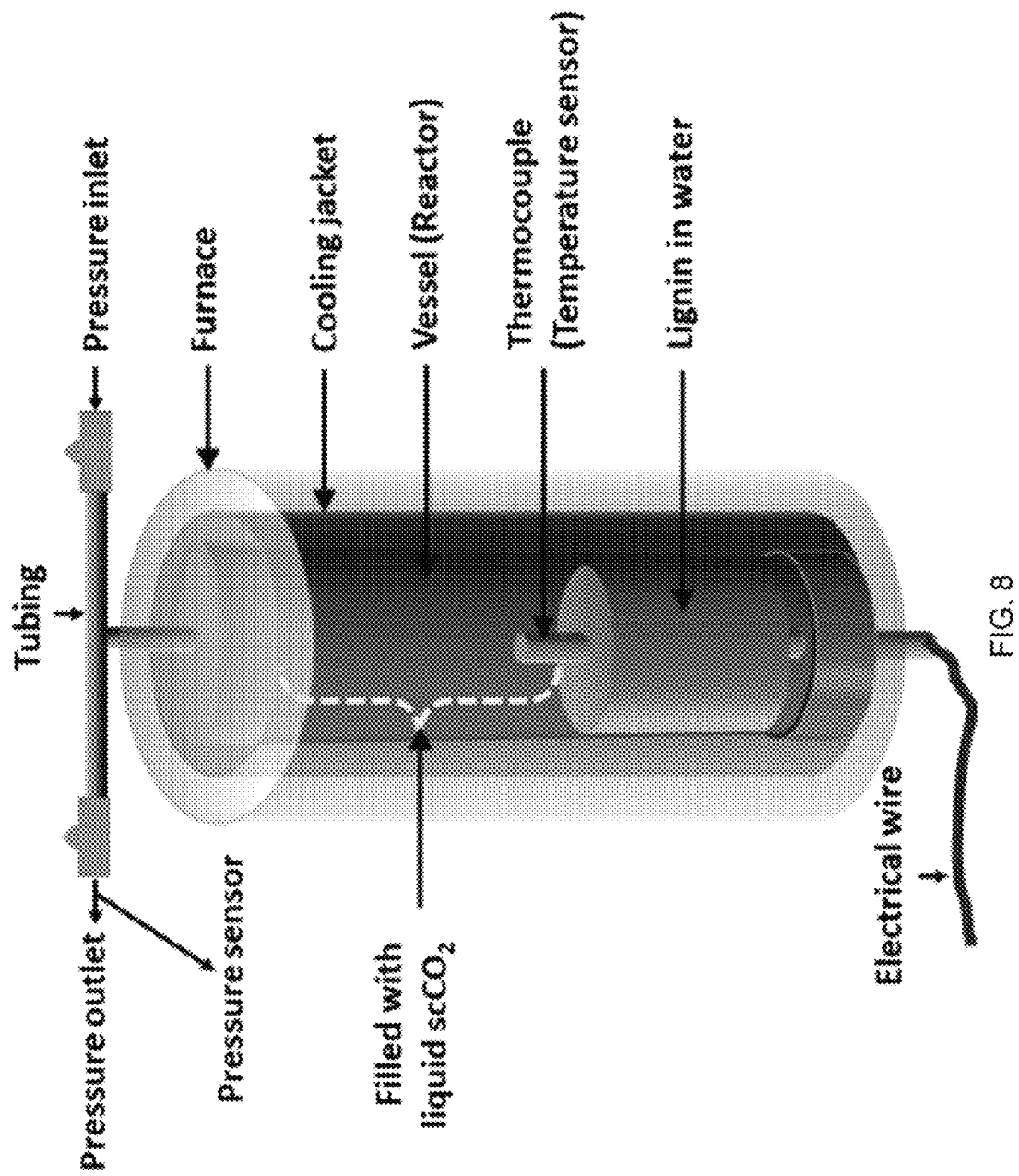
FIG. 8 is a pictorial representation of a batch reactor in accordance with an illustrative aspect of the present disclosure.
Figure 12:
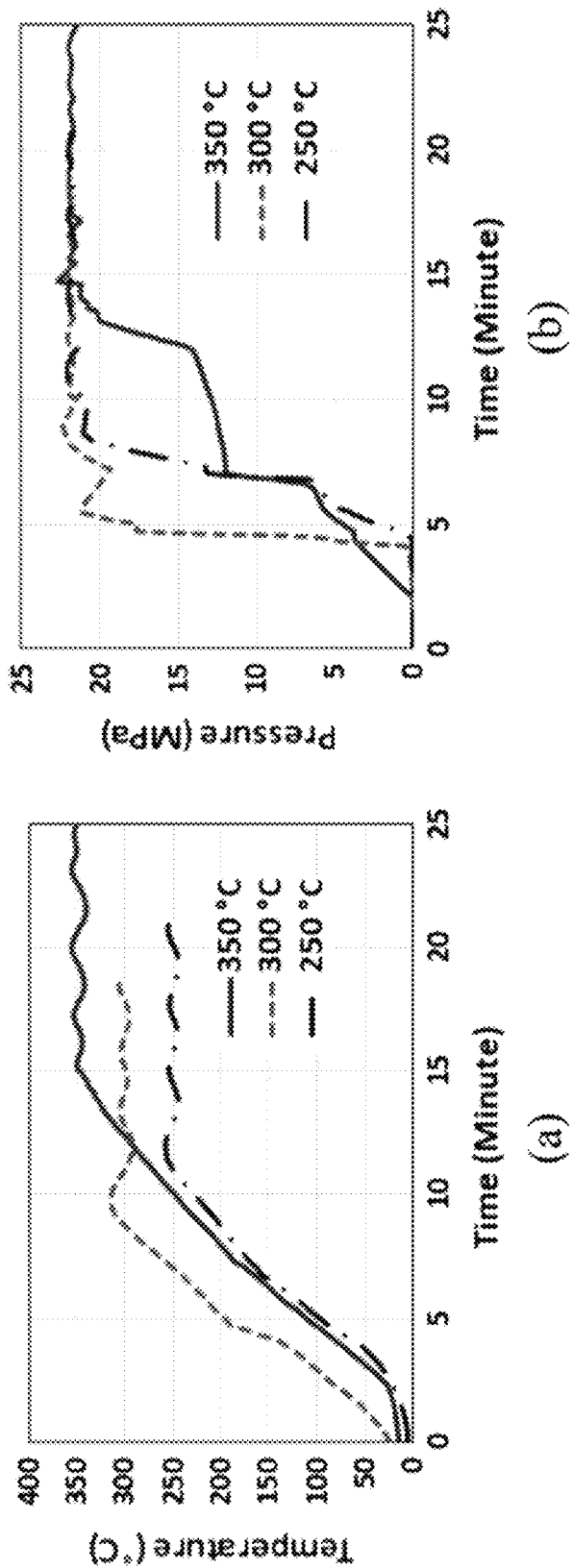
FIG. 12 is a pictorial representation of temperature (a) and pressure (b) for 10 min of residence time at 250, 300, and 350° C. in accordance with an illustrative aspect of the present disclosure.

The treatment of alkali lignin at sub- and supercritical conditions in a temperature range of 250-350° C. can be carried out in a stainless steel high-pressure vessel (316 SS) having a capacity of 12 mL with a pressure tolerance of up to 103 MPa (FIG. 1). A type K thermocouple can be inserted through the bottom of the vessel to measure the temperature inside the vessel by an AMProbe temperature meter. The internal pressure can be controlled by the pressure sensor connected to the monitor. To achieve reproducible synthesis conditions, the temperature ramp can be adjusted in each experiment. The batch reactor for the hydrothermal procedure is shown in FIG. 8. According to exemplary aspects of the present disclosure, 0.10, 0.25, and 0.50 g of lignin is placed inside the vessel, followed by addition of the varying amounts (2, 4, 6, or 8 mL) of deionized water. The vessel with the inserted thermocouple is sealed and placed into the split Carbolyte furnace for hydrothermal treatment. In order to reach the targeted temperature within the shortest period of time, the initial setup temperature of the Carbolyte temperature controller can be adjusted to 700° C. with a ramp rate of 100° C./min. Depending on the synthesis conditions, after 5-10 min (FIG. 12) the temperature can be adjusted to the required value. The pressure inside the vessel (22.063 MPa) can be maintained by a Teledyne syringe pump 260D pressurized with liquid $CO_2$. When the pressure and temperature requirements are met, a stopwatch can be used to record the residence time. During this time period, the temperature and pressure inside the vessel is continuously monitored by an AMProbe temperature controller and a pressure sensor, respectively (FIG. 12). After 10 min, the furnace can be turned off and the pressure released. The reaction vessel can then be cooled down by immersing it into cold water. The liquid that comes out through the pressure valve during the pressure adjustment is collected and combined with the liquid phase from the pressure vessel to measure the final weight.

After the lignin treatment in a mixture of subcr$H_2$O and sc$CO_2$, the liquid organic phase can be separated from the solid phase by centrifugation. The weight of the solid phase before and after hydrothermal reforming in sc$CO_2$ can be measured gravimetrically. In the experimental temperature range of 250-350° C. the alkali lignin consumption is ~50%. Separation of the liquid organic phase from aqueous phase can be performed by liquid-liquid extraction (LLE) using dichloromethane (DCM). In a first step of extraction, 10 lL of acetic acid is added to every 1.0 mL of a liquid sample for adjustment of the pH value to ~2.0. Then the recovery standard (4-chloro-acetophenone) can be added enabling to monitor and correct for losses during the extraction. The sample can be then extracted three times with 1.0 mL of DCM with vigorous shaking. After the DCM (bottom layer) and the water (top layer) phases are separated, the bottom layers are collected and combined, and then the 4-chloroacetophenone is added to the sample for quantitative analysis.

The GC-MS analysis of the liquid organic samples can be performed using GCMS-QP2010 Ultra Gas Chromatograph/Mass Spectrometer (GCMS) from Shimadzu. All injections (1.0 lL) can be conducted in a split mode with sampling time of 1 min. A 30 m Rxi-5Sil MS fused silica column (Restek Corporation, Bellefonte, Pa., USA) with a 0.25 mm I.D. and a 0.25 lm film thickness can be used for all separations. Ultra-pure helium (99.999%) can be used as a carrier gas with a constant flow rate of 5.8 mL min. The initial oven temperature can be set up to 50° C. and held up for 1.0 min, then ramped to 280° C. with a rate of 10° C./min. This step can be followed by a ramp to 320° C. with a rate of 20° C. and 5 min dwell time. The injector and the transfer line temperatures are set up to 250 and 300° C., respectively. All the MS data is acquired in a total ion current (TIC) mode with a mass range of 45-500 m/z. The relative yield (R.Y.) of the phenolic products is defined as follows:

$$R.Y. = \frac{\text{Area under the } GCMS \text{ peak}}{\text{Total area of the } GCMS \text{ peaks}} 100\%$$

In terms of the total yield and mass balance, only solid and liquid phases is taken into consideration. The mass of the gases, such as $CH_4$, CO, $CO_2$, or $H_2$ that are usually produced at the temperatures above the experimental temperature range (250-350° C.) is considered negligible in comparison with the weight of the solid and liquid products. To confirm the reproducibility of the results, the experiments can be repeated three times for the same sample and the standard deviation is estimated in the range of 0.5-2.6%.

A Total Organic carbon (TOC) analyzer TOC-LCPN from Shimadzu can be used for characterization of the total organic carbon in the sample. The TOC-L can be calibrated using potassium hydrogen phthalate (KHP) from 0 mg/L to 1000 mg/L. In order to obtain the results in the calibration range, the samples are diluted 30 times prior to the measurement.

In the experimental temperature range of 250-350° C. (FIG. 12) and constant pressure of 22.063 MPa carbon dioxide forms a supercritical fluid and water is present in a subcritical state. Complex interactions between two fluids and the properties of the supercritical carbon dioxide in sub- or supercritical water affect the mutual solubility of the reagents, chemical reactions, and kinetics of the catalytic processes that take place on the lignin surface and within its porous structure. Furthermore, the phenolic species produced during hydrothermal treatment are known to catalyze lignin polymerization, which makes the analysis of lignin liquefaction even more complicated.

Figure 13:
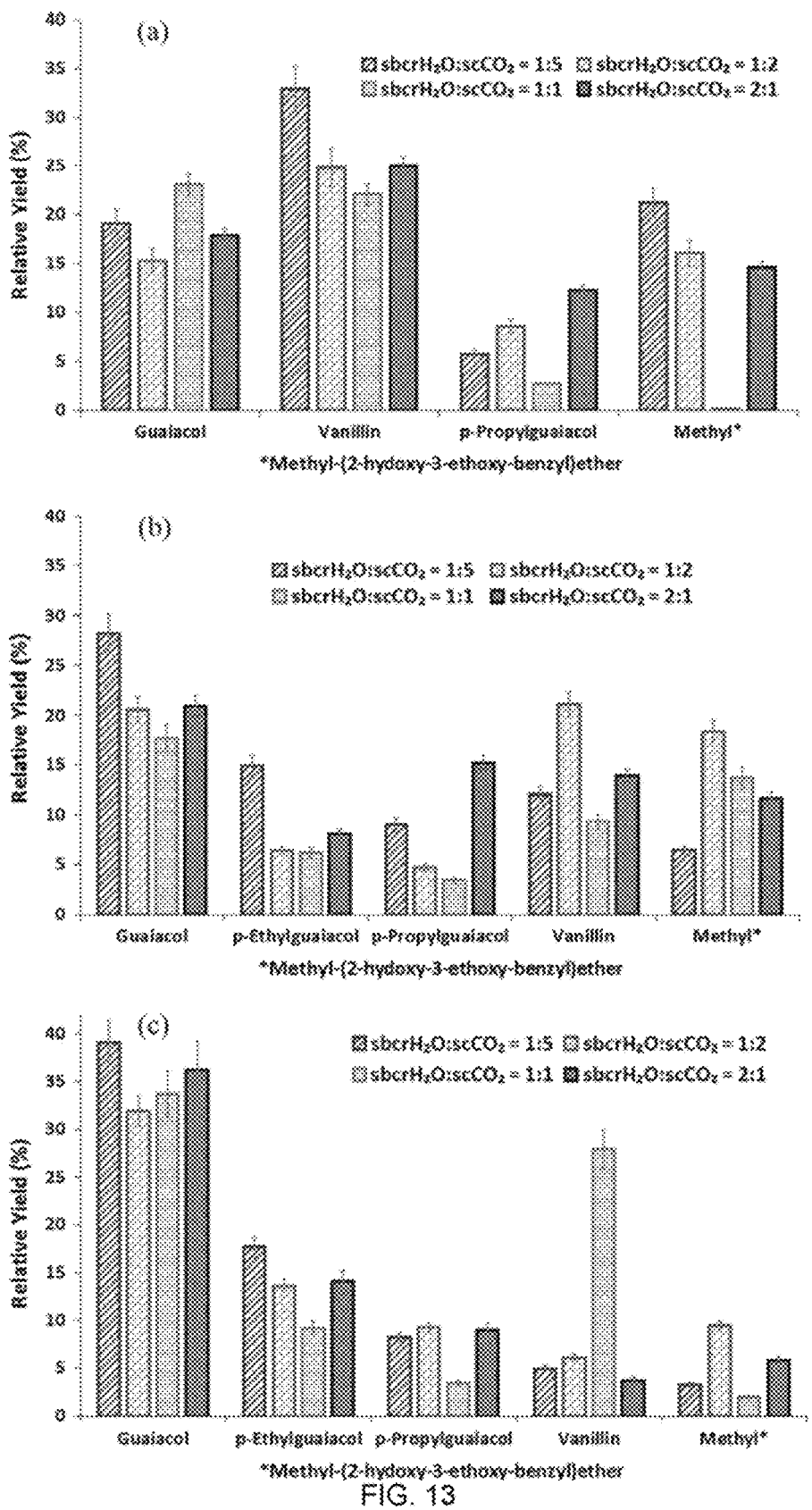
FIG. 13 is a pictorial representation of GC-MS analysis data of the products formed after lignin hydrothermal treatment with $scCO_2$-$sbcrH_2O$ ratios (1:5, 1:2, 1:1, and 2:1) at (a) 250° C., (b) 300° C., and (c) 350° C. in accordance with an illustrative aspect of the present disclosure.

The comparative GC-MS results for the lignin decomposition products formed in $sbcrH_2O$ and $scCO_2$ fluid mixtures within a temperature range of 250-350° C. and 10 min residence time (FIG. 13) provide an evidence for selective production of specific phenolic compounds. The yield of four/five major phenolic products is considered in regard to the lignin liquefaction at $sbcrH_2O$ and $scCO_2$ ratios (1:5, 1:2, 1:1, and 2:1) and different temperatures, such as 250, 300, and 350° C. At the lowest temperature of 250° C. (FIG. 139a)) and the highest amount of $scCO_2$ ($sbcrH_2O$:$scCO_2$=1:5), vanillin is found as the major reaction product with the relative yield of ~33%. The yields of two other phenolic products, specifically guaiacol and methyl-(2-hydroxy-3-ethoxy-benzyl) ether are up to 19% and 21%, respectively. Vanillin and methyl-(2-hydroxy-3-ethoxy-benzyl) ether show the decreasing trend when the amount of $scCO_2$ decreases (except at $sbcrH_2O$:$scCO_2$=2:1 which could be due to the catalytic effect of $scCO_2$). The highest yields of the major phenolic products are found at $sbcrH_2O$:$scCO_2$=1:5 ratio (FIG. 13(a)).

At 300° C. (FIG. 13(b)), for $sbcrH_2O$-$scCO_2$=1:5 ratio, guaiacol has the highest yield of ~28%. Compared to the $scCO_2$ hydrothermal treatment of lignin at 250° C., the temperature increase to 300° C. causes a significant increase in guaiacol concentration (~47%). In addition, a new product, p-ethylguaiacol, is observed at this temperature. Furthermore, an increase in the amount of $scCO_2$ (two and five times higher than $sbcrH_2O$) yields a higher amount of phenols (~40%). Interestingly, at 300° C., compared to 250° C., the relative yield of vanillin decreases by 63% indicating the change in selectivity from vanillin to guaiacol.

At 350° C., the highest relative yield of guaiacol (~39%) is obtained at $sbcrH_2O$-$scCO_2$=1:5 ratio. A further increase in the guaiacol relative yield at 350° C. by 38% and 104% is observed when compared to the yield at 300° C. and 250° C., respectively (FIG. 13(c)). Noted here is that at 350° C., when the amount of $sbcrH_2O$ is higher, the yield of guaiacol becomes higher (~36%); however, it does not exceed the yield (~39%) found at $sbcrH_2O$:$scCO_2$=1:5 ratio.

Considering the selectivity, each temperature results in a specific phenolic compound. For example, at 250° C. (FIG. 13(a)) vanillin has the yield of ~33%, whereas, at 300° C. (FIG. 13(b)), guaiacol has the highest relative abundance (~28%). However, at 350° C. (FIG. 13(c)), the amount of guaiacol is significantly higher (~39%) when a large amount of $scCO_2$ at the volume ratio of $sbcrH_2O$:$scCO_2$=1:5 is used.

The observed difference at $sbcrH_2O$:$scCO_2$ ratios at all temperatures with respect to a higher selectivity toward guaiacols can be explained by the presence of carbon dioxide as an acidic homogeneous catalyst that affects the kinetic pathways of lignin depolymerization and prevents the corresponding phenolic products from repolymerization.

Figure 14:
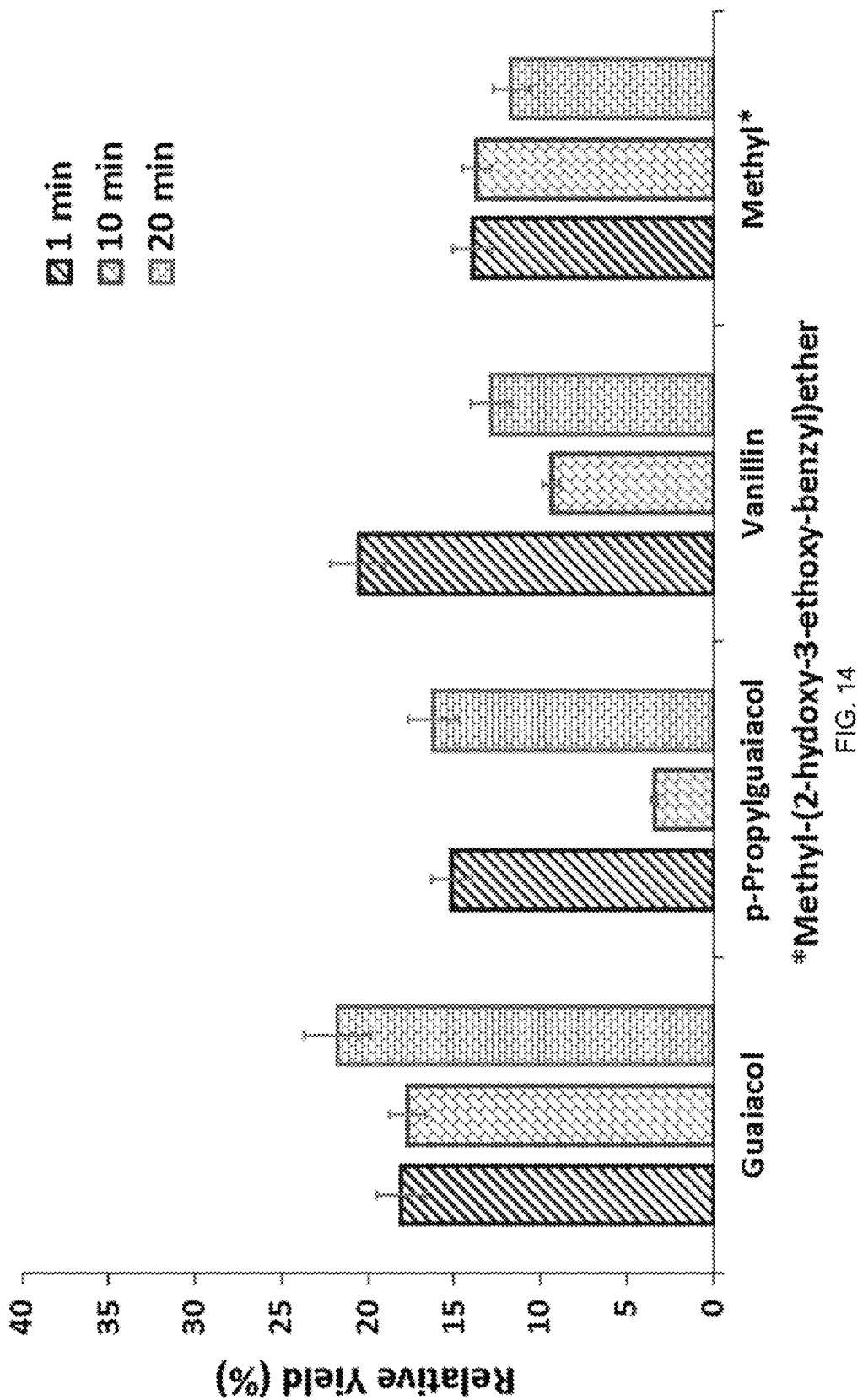
FIG. 14 is a pictorial representation of GC-MS analysis data of the products formed after lignin hydrothermal treatment for different residence times at 300° C. and lignin loading of 0.10 g at a constant $scCO_2$:$sbcrH_2O$=1:1 volume ratio in accordance with an illustrative aspect of the present disclosure.

Evaluation of the selectivity toward formation of the specific phenolic products at various residence times (1, 10, and 20 min) can be performed at 300° C. 0.1 g lignin loading. At 1 min residence time the relative yield of vanillin is the highest (~21%). However, when the residence time increases to 10 and then to 20 min (FIG. 14), the relative yield of guaiacol becomes higher resulting in ~18%, and ~22%, respectively. However, only vanillin shows an exception demonstrating a higher relative yield at 1 min residence time, indicating the change in selectivity.

Figure 15:
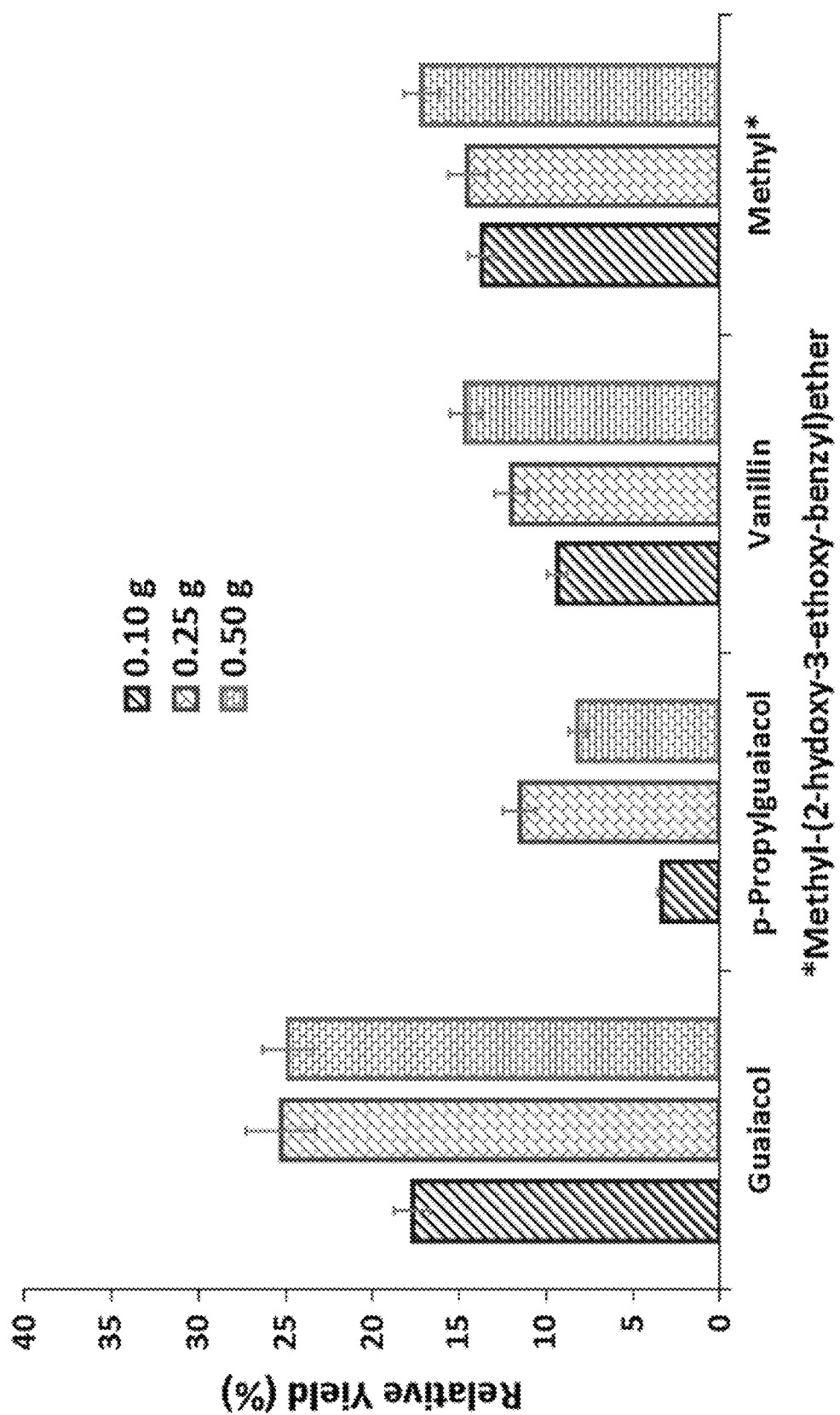
FIG. 15 is a pictorial representation of GC-MS analysis data of the products identified after the scCO2 hydrothermal treatment for different lignin loadings (0.10, 0.25, and 0.50 g) at 300° C., 10 min residence time, and constant $sbcrH_2O$-$scCO_2$=1:1 volume ratio in accordance with an illustrative aspect of the present disclosure.

The results of the alkali lignin decomposition in $scCO_2$-assisted hydrothermal environment are illustrated for different lignin loadings (0.10, 0.25, and 0.50 g), while maintaining constant temperature (300° C.), residence time (10 min), and $sbcrH_2O$-$scCO_2$=1:1 ratio are presented in FIG. 15. As expected, the produced amounts of guaiacol, vanillin and methyl-(2-hydroxy-3-ethoxy-benzyl) ether increase with lignin loadings. However, the guaiacol demonstrated a different trend indicating that significant increase in relative yield (from 17% to 25%) is observed while changing the lignin loading from 0.1 to 0.25 g. Further increase in lignin loading to 0.5 g does not increase the relative yield of guaiacol. A different outcome is detected for p-propylguaiacol which is produced in the highest amount of ~12% at the medium lignin loading of 0.25 g. Regarding the total yield of the phenolic compounds, the variation of the lignin loading results in formation of ~44%, ~63%, and ~65% at 0.10, 0.25, and 0.50 g loadings of lignin, respectively, which is an expected outcome considering that formation of phenolic monomers is proportional to the total amount of lignin in the reaction mixture.

Figure 16:
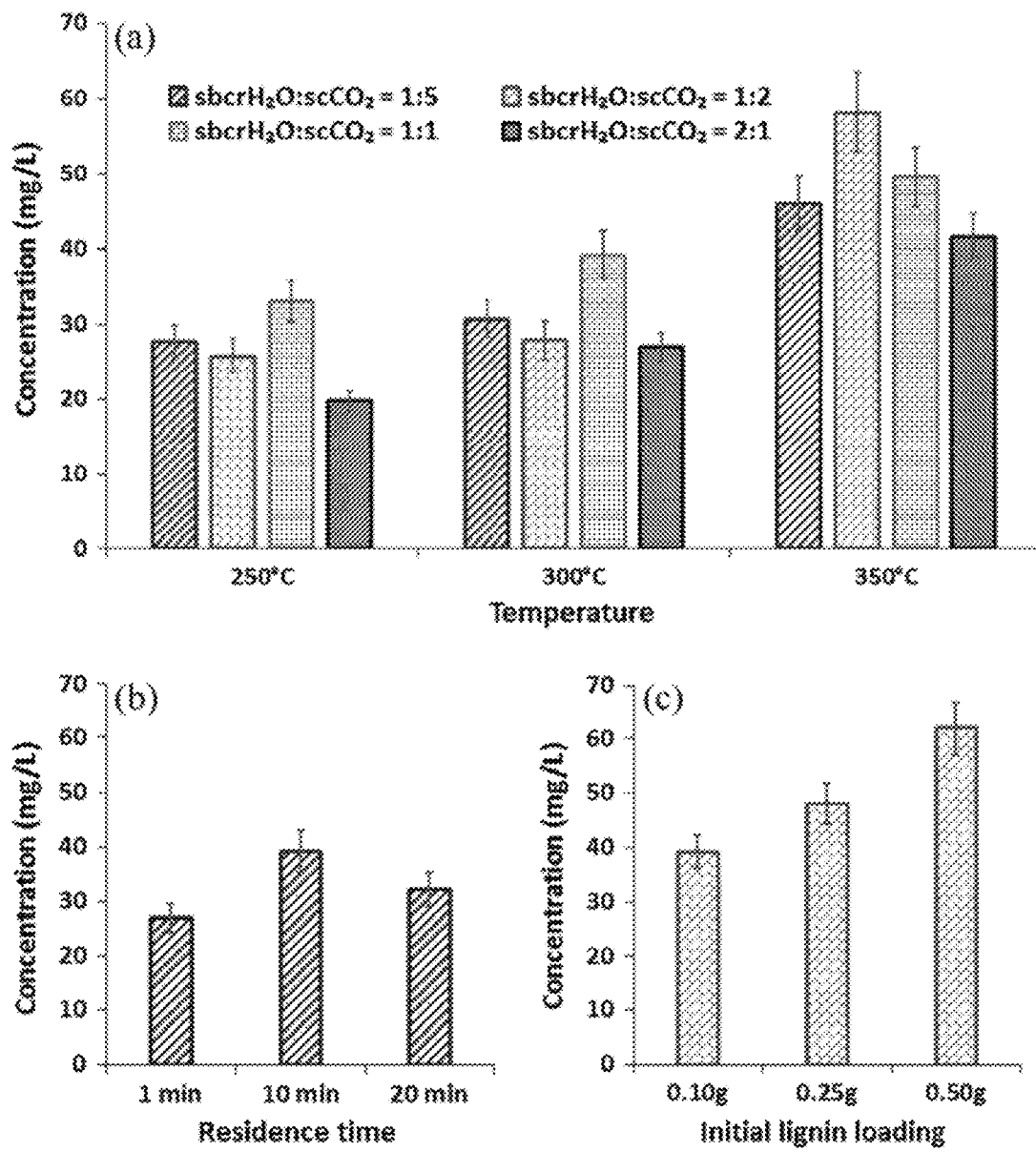
FIG. 16 is a pictorial representation of the total organic carbon (TOC) concentration for different: (a) Treatment temperatures at constant $sbcrH_2O$-$scCO_2$=1:1 ratio, lignin loading (0.10 g) and residence time (10 min), (b) residence times at constant temperature (300° C.), $sbcrH_2O$-$scCO_2$=1:1 ratio, and lignin loading (0.10 g), and (c) lignin loading at constant temperature (300° C.), $sbcrH_2O$- scCO$_2$=1:1 ratio, and residence time (10 min) in accordance with an illustrative aspect of the present disclosure.

The results of the TOC evaluation for different sbcrH$_2$O-scCO$_2$ ratios (FIG. 16) illustrate that the concentration of the total organic carbon increases with temperature. At 350° C. (FIG. 16(a)), the highest amount of carbon (58.25 mg/L) is detected which indicates that the maximum conversion of lignin takes place compared to 250° C. and 300° C. However, the 10 min residence time results in the highest amount of total organic carbon (FIG. 16(b)). On the other hand, less amount of organic carbon produced at larger residence time (20 min) can be attributed to the repolymerization of the monomeric phenols. Furthermore, the higher amount of lignin in the reaction mixture generates higher amounts of the organic carbon during the scCO$_2$ hydrothermal treatment (FIG. 16(c)). Overall, the TOC results obtained by fixing all the parameters of the reaction mixture except one (FIG. 16(a)-(c)) are in good correlation with the GC-MS results and demonstrate the importance of parameters optimization providing a reasonable comparison of the TOC amounts in the liquid phase in regard to the scCO$_2$-assisted hydrothermal process.

The properties of sub- or supercritical water as a strong oxidizing agent are known. However, these properties do not allow to achieve selective synthesis of phenolic products from lignin due to strong repolymerization that results in formation of higher molecular weight products and decreases the reaction selectivity. In presence of scCO$_2$ performing as an acidic catalyst without mass-transport limitations, the repolymerization process is eliminated, which is also confirmed by the absence of tar or char in the experimental temperature range of 250-300° C. The presence of supercritical carbon dioxide as a homogeneous catalyst increases the acidity of the reaction media, promoting the β-O-4 bond scission. During this process lignin as an aromatic heteropolymer forms various phenols and methoxy phenols through the hydrolysis of the ether β-O-4 bond. Degradation of lignin can proceed further through hydrolysis of methoxy groups, without compromising the stability of the benzene ring itself. The efficiency of this reaction is enhanced due to the properties of the supercritical CO$_2$ fluid that can penetrate small pores of lignin (<250 nm) without mass transport limitations.

Figure 17:
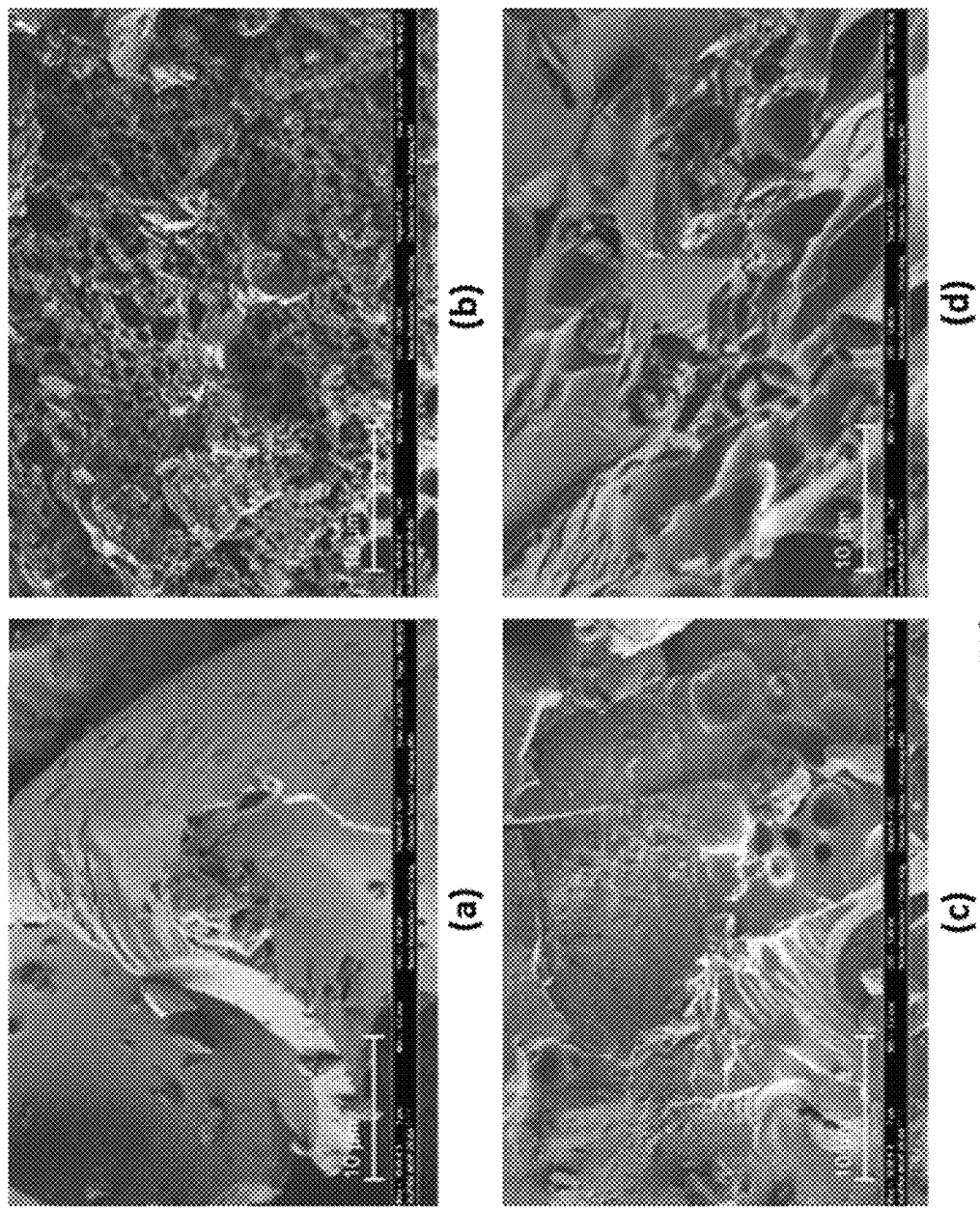
FIG. 17 is a pictorial representation of SEM images of raw lignin and decomposed lignin in presence of scCO$_2$-sbcrH$_2$O: (a) raw lignin, (b) 250° C., (c) 300° C., and (d) 350° C. at sbcrH$_2$O:scCO$_2$=1:1 ratio, and 10 min residence time in accordance with an illustrative aspect of the present disclosure.

The amount of solid phase left over after decomposition of the alkali lignin in scCO$_2$-assisted hydrothermal process can be evaluated by the gravimetric analysis. The results indicate that the amount of lignin left over in the reactor is about 75% at 250° C. and gradually decreases with temperature reaching ~62% and ~50% at 300° C. and 350° C., respectively. These values are supported by comparing the SEM images of the untreated raw lignin and the lignin after the scCO$_2$-assisted hydrothermal treatment (FIG. 17) at 250° C., 10 min residence time, and sbcrH$_2$O:scCO$_2$=1:1 ratio. In comparison with the untreated lignin (FIG. 17(a)) that does not show any porosity, the structure of lignin after treatment at 250° C. has different morphology and demonstrates significant effect of scCO$_2$ in combination with sbcrH$_2$O. At 300° C., lignin starts to melt and the surface porosity is not visible anymore.

This process continues at 350° C., demonstrating a rigid structure of the solid phase leftover from lignin. Despite previous tar or char formation being detected at these temperatures, no evidence of tar or char is found at 250 or 300° C. At 350° C. a small amount of char can be found in the lignin sample emphasizing that the char formation is promoted at higher temperatures. In order to minimize or eliminate the amount of the solid lignin phase in the process of scCO$_2$ hydrothermal reforming, a circulation type of the reactor with continuous flow of the lignin-water mixtures should be considered in future along with the detailed analysis of the selectivity mechanisms toward formation of specific phenolic compounds within a continuous flow reactor system.

3.6.3 Example 3

A biomass can be selectively depolymerized using a combination of a supercritical carbon dioxide fluid in combination with sub-, near-, or supercritical water. Improved selectivity toward formation of specific phenolic product or a group of related specific products is obtained according to the present disclosure that includes a regulation of the ratio between supercritical carbon dioxide and water in subcritical, near-critical, or supercritical state. By using supercritical carbon dioxide as a green solvent and a homogeneous catalyst for selective liquefaction of the biomass or lignin, the selective yield of a specific phenolic product or a group of chemically related specific phenolic products can be significantly enhanced. The parameters, such as temperature and pressure can be used for selective yield optimization resulting in production of one specific phenolic product or a group of chemically related specific phenolic products.

A biomass or lignocellulosic biomass comprises cellulose, hemicellulose, and lignin. For the selective yield of the specific phenolic product or a group of chemically related specific phenolic products, the temperature is preferably held at least 100° C., preferably at least 150° C., preferably at least 200° C. As such, these temperatures may be seen as preferred minimum levels for the selective liquefaction of biomass according to the present disclosure.

Selective liquefaction of the biomass in presence of the said supercritical carbon dioxide and water in subcritical, near-critical, or supercritical state may take place in different types of the reactors (FIG. 8), such as a batch single-run reactor and a flow reactor or a circulation reactor in which the biomass can be fed to the reactor continuously. In all these cases the temperature control can be maintained allowing preferably fast biomass or lignin heating and preferably fast liquefied product cooling, thus preventing repolymerization and selectivity loss.

For the selective yield of the specific phenolic product or a group of chemically related specific phenolic products, the temperature ramp should preferably be held at least 100° C., and preferably at least 150° C. followed by the residence time of at least 1 minute, preferably at least 10 minutes, preferably at least 15 minutes. These heating ramp rates and residence times are preferred minimum levels, in at least one aspect of the disclosure, for the selective liquefaction of biomass.

For extraction of a specific liquid phenolic product or a group of chemically related specific phenolic products selectively produced from biomass or lignin, an approach known as liquid-liquid extraction can be used. In this approach, a heterogeneous/homogeneous mixture of specific phenolic product or a group of chemically related specific phenolic products, water and particulates from biomass or lignin (FIG. 1(b)) is centrifuged. Then, 10 μL of acetic acid is added per 1 mL of a liquid sample to assure the acidity level at pH~4. The recovery standard (4-chloroacetophenon) is added enabling to monitor and correct the losses during the extraction. The samples can then be extracted three times with 1 mL of dichloromethane (DCM). After the separation of the bottom DCM phase and the top water phase (FIG.

1(b), center), the bottom layers can be separated and combined for further chemical analysis.

3.6.4 Example 4

The present disclosure is directed to providing a process for selective liquefaction of biomass and/or lignin in presence of supercritical carbon dioxide, water at subcritical, near-critical, or supercritical conditions, in combination with one heterogeneous inorganic catalyst or a mixture of heterogeneous inorganic catalysts (e.g., metal oxides, spinels, fluorites, perovskites, etc.) producing a specific phenolic product or a specific group of chemically related phenolic products. In one example, a method for selective liquefaction of biomass and/or lignin wherein the biomass and/or lignin are subjected to liquefaction by treatment with water at subcritical, near-critical, or supercritical conditions, and one heterogeneous inorganic catalyst or a mixture of heterogeneous inorganic catalysts achieved by pressurizing the vessel with liquid or gaseous carbon dioxide and reaching a supercritical carbon dioxide fluid condition within the pressure vessel.

According to one specific embodiment, the method includes a step when the biomass and/or lignin subjected to liquefaction by treatment with water at subcritical, near-critical, or supercritical conditions and one heterogeneous inorganic catalyst or a mixture of heterogeneous inorganic catalysts achieved by pressurizing the vessel with carbon dioxide, is subjected to fast heating in the beginning of the process to prevent repolymerization of the phenolic products. Another exemplary step of the method includes the biomass and/or lignin subjected to liquefaction by treatment with water at subcritical, near-critical, or supercritical conditions achieved by pressurizing the said water with supercritical carbon dioxide in presence of one heterogeneous inorganic catalyst or a mixture of heterogeneous inorganic catalysts is subjected to fast cooling at the end of the process to prevent repolymerization of the phenolic products. According to one specific aspect, the amount of water at subcritical, near-critical, or supercritical conditions in presence of one heterogeneous inorganic catalyst or a mixture of heterogeneous inorganic catalysts can vary in relation to the amount of biomass and/or lignin subjected to liquefaction. According to another specific aspect, the amount of supercritical carbon dioxide in presence of one heterogeneous inorganic catalyst or a mixture of heterogeneous inorganic catalysts can vary in relation to the amount of biomass and/or lignin subjected to liquefaction and water at subcritical, near-critical, or supercritical conditions. In yet another aspect, the amount of one heterogeneous inorganic catalyst or a mixture of heterogeneous inorganic catalysts can vary in relation to the amount of biomass and/or lignin subjected to liquefaction in presence of supercritical carbon dioxide, and water at subcritical, near-critical, or supercritical conditions.

3.6.5 Example 5

The present disclosure is directed to methods in selective synthesis of biomass or biomass derived products, e.g. lignin, in presence of supercritical carbon dioxide fluid in a mixture with sub-, near-, or supercritical water combined with a various heterogeneneous inorganic catalyst. In this regard, our new approach validates that the selectivity of the biomass or biomass-related product liquefaction can be tuned by the changes in the sub-, near-, or supercritical water, the supercritical carbon dioxide, and catalyst amounts relative to the amount of the biomass or lignin used for the experiment. In at least one exemplary aspect, 0.1 g of lignin, 6 mL of deionized water, and 0.1 g of Nickel Oxide (NiO) are placed inside the vessel (FIG. 1(a)). The vessel with the inserted thermocouple is sealed and placed into the split Carbolyte furnace for the treatment. In order to reach the targeted temperature within the shortest period of time, the initial set-up temperature of the Carbolyte temperature controller is adjusted to 650° C. with a high ramp rate of 100° C./min. Depending on the synthesis conditions, after 2-5 min the temperature can be adjusted to the required value. The pressure inside the vessel (22.063 MPa) can be maintained by a Teledyne syringe pump 260D pre-pressurized with $CO_2$ or $N_2$. When the pressure and the temperature requirements are met, a stopwatch can be used to record the residence time. During this time period, the temperature and the pressure inside the vessel can be continuously monitored. After 10 minutes, the furnace is turned off and the pressure is released. The vessel then can be quenched by immersion into cold water.

Figure 10:
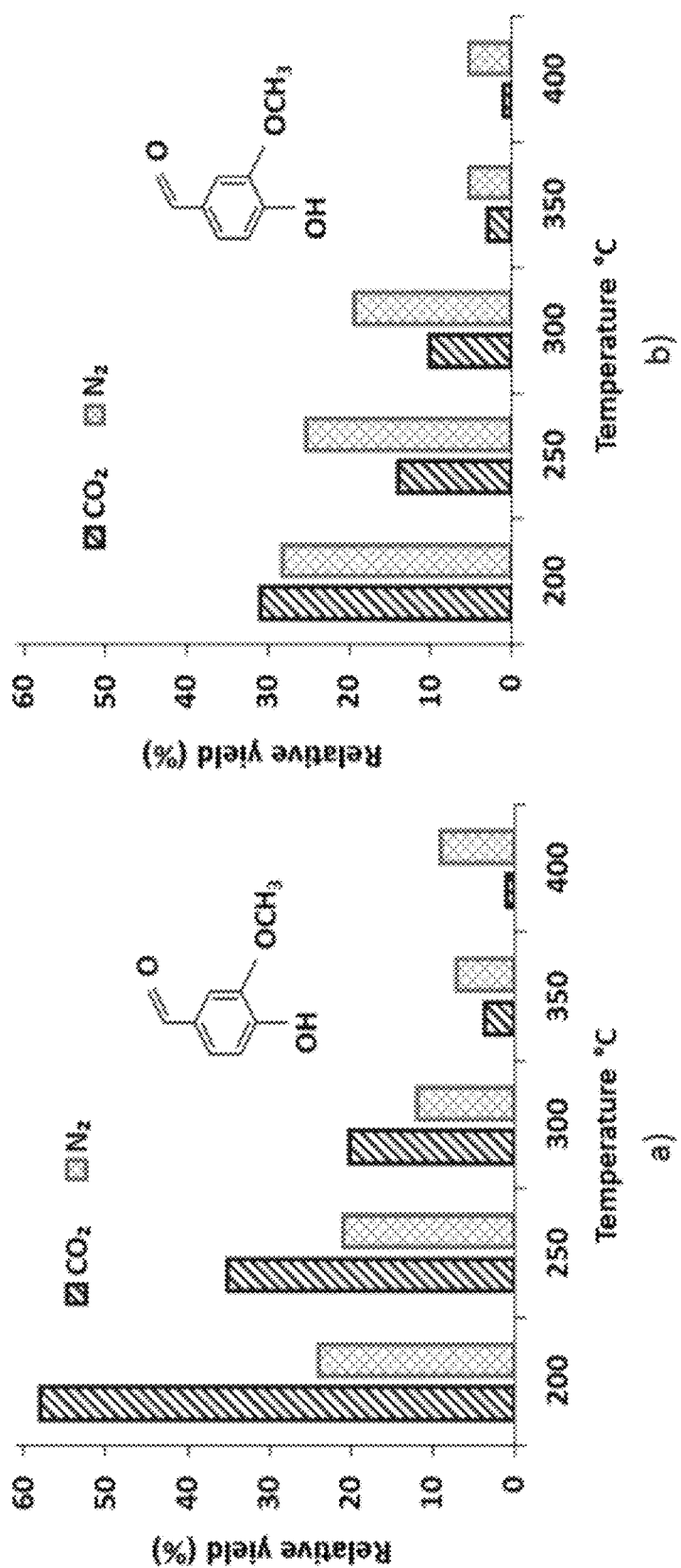
FIG. 10 is a pictorial representation of an example of the relative yield of the selectively synthesized 4-hydroxy-3-methoxy-benzaldehyde in carbon dioxide supercritical fluid in comparison to nitrogen in presence of sub-, near-, and super-critical water and a heterogeneous catalyst: (a) Nickel oxide catalyst and (b) Ceria doped Scandia stabilized Zirconia (CeScSZ) fluorite in accordance with an illustrative aspect of the present disclosure.

The results of the GC-MS analysis are presented in FIG. 10. The results illustrate that in comparison to nitrogen, the supercritical carbon dioxide in presence of nickel oxide as a heterogeneous catalyst significantly increases the relative yield of predominantly one phenolic compound, specifically 4-hydroxy-3-methoxy-benzaldehyde (~58 wt. %) with the total yield of other chemically related phenolic compounds in the liquefied lignin samples up to 85 wt. % (FIG. 10(a)). An example of the relative yield of the selectively synthesized 4-hydroxy-3-methoxybenzaldehyde in carbon dioxide supercritical fluid in comparison to nitrogen in presence of sub-, near, and supercritical water and a heterogeneous catalyst of Ceria doped Scandia stabilized Zirconia (CeScSZ) fluorite is shown in FIG. 10(b).

Figure 11:
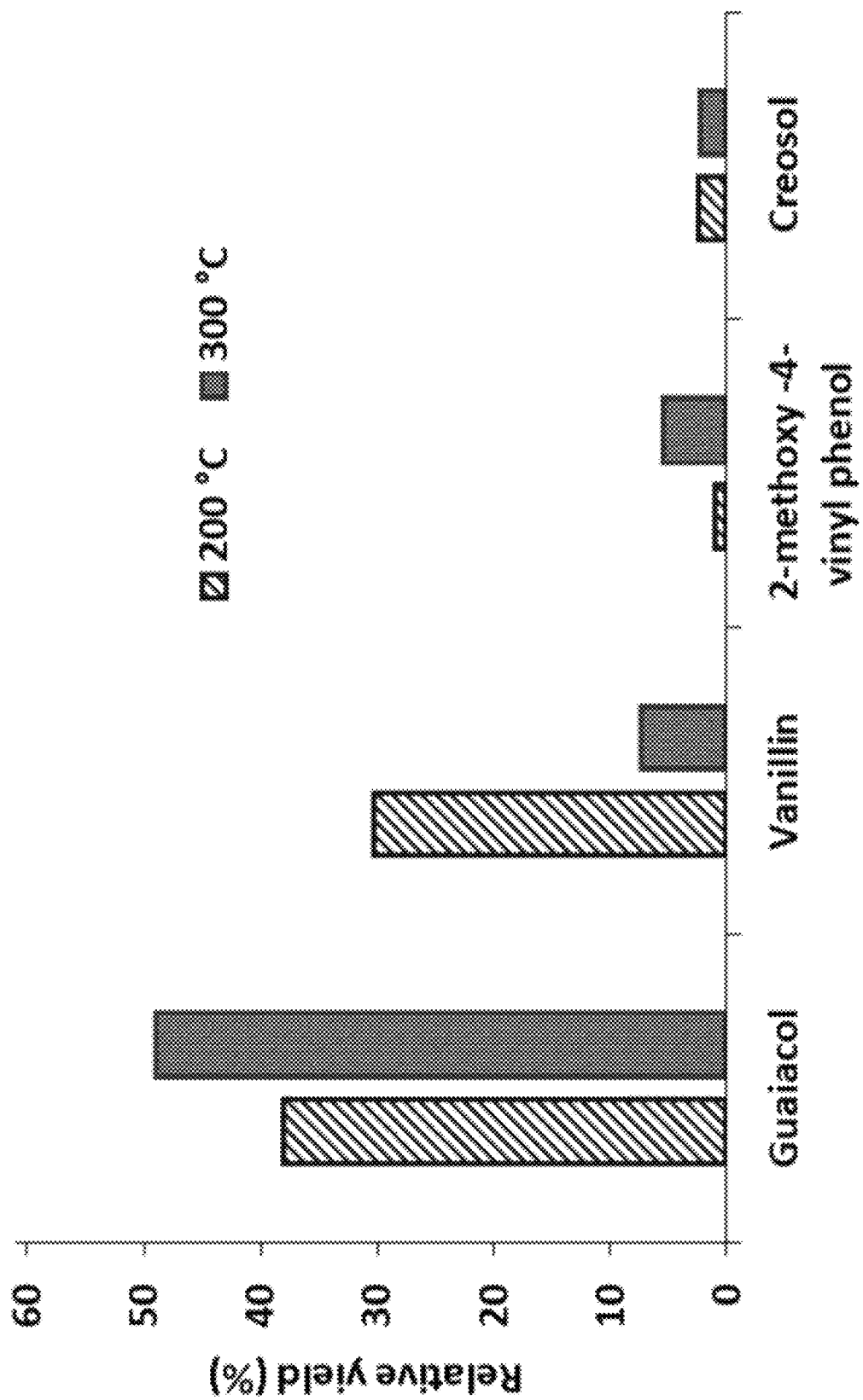
FIG. 11 is a pictorial representation of an example of the relative yield of the major phenolic compounds synthesized in carbon dioxide supercritical fluid and presence of subcritical water in combination of a heterogeneous catalyst: $SmNi_{0.1}Co_{0.9}O_{3-\delta}$ catalyst in accordance with an illustrative aspect of the present disclosure.

The samarium-based materials with a targeted composition of $SmNi_xCo_{1-x}O_{3-\delta}$, where x=0.1 was synthesized using a modified nitrate-glycine Pechini method and sintered at 900° C. And characterized by The X-ray diffraction analysis. The treatment of alkali lignin in sub-and supercritical conditions and temperature range of 200-400° C. in presence of Sm perovskites as heterogeneous was carried out in a stainless steel high-pressure reactor, and the organic phase collected after the $scCO_2$ hydrothermal treatment after separating from the aqueous phase by liquid-liquid extraction (LLE). The relative yield of each compound obtained for GC-MS analysis was calculated as a percent ratio between the areas under the peak of this compound divided by the total area of the peaks. The GC-MS analysis of the organic phase produced after the hydrothermal liquefaction demonstrates that for temperatures 200 and 300° C. the presence of $scCO_2$ is beneficial in regard to the relative yield of the phenolic products. The highest relative yield of guaiacol ~49% is observed in the case of 300° C. while ~38% at 200° C. (FIG. 11).

4.0. Conclusions

The effect of temperature at a constant pressure, short residence time, and fixed amount of alkali lignin sample on the selectivity and yield of the phenolic products from the hydrothermal reforming of alkali lignin is disclosed in a mixture of sub- and supercritical fluids ($H_2O$ mixed with $CO_2$ or $N_2$).

Depending on the hydrothermal treatment conditions, the lignin samples produced different phenolic compounds such as guaiacol and its homologs, homovanillic acid, quaiacyl carbonyls, guaiacyl dimers, phenol and cresols as shown by GC-MS analysis. Verifying this information, the TCA analyses of unextracted liquid phases demonstrates the increase of volatilizable compound concentration with temperature and dependence on the presence of $CO_2$. The increase of volatilizable content of the liquid phase products at higher temperature occurs at the expense of the recalcitrant pyrolyzed carbon or "char".

The phenol-based liquid organic products of the alkali lignin degradation at near critical temperatures in presence of in $H_2O$—$CO_2$ shows a significant difference in comparison to $H_2O$—$N_2$ at 300° C., apparently due to a catalytic effect of carbon dioxide as an acid catalyst. At this temperature and pressure, a higher abundance of quaiacol derivatives is observed in the liquid phase. Similarly, the TCA analyses confirms increases content of the volatile fraction in the $CO_2$-treated samples. Finally the solid phase obtained at high temperatures with $CO_2$ shows a significant content of phenolics which are not detected in either raw lignin or in the solid products of its decomposition at lower temperatures. The effect of $CO_2$ vs. $N_2$ pressurization evaluated in the present disclosure has significant implications for the selective synthesis of phenolic compounds and their use in synthesis of polymers with desirable properties.

LIST OF REFERENCES CITED

The following documents are cited in this application, and are incorporated herein in their entirety:

1. T. Yoshikawa, S. Shinohara, T. Yagi, N. Ryumon, Y. Nakasaka, T. Tago, App. Cat. B: Env. 146, 289-297 (2014).
2. M. Hofrichter, Enzyme and Microbial Tech 30 454-466 (2002).
3. P. Parpot, A. Bettencourt, A. Carvalho, and E. Belgsir, J. of App. Electrochemistry 30, 727-731 (2000).
4. T. Yong, Y. Matsumura, Industrial & Engineering Chemistry Research, 52, 5626-5639, (2013).
5. F. Tabasinejad, R. G. Moore, S. A. Mehta, K. C. Van Fraassen, Y. Barzin, J. A. Rushing, Ind. & Eng. Chem. Res. 50, 4029-4041 (2011).
6. Finch, K.; Richards, R.; Richel, A.; Medvedovici, A.; Gheorghe, N.; Verzui, M.; Coman, S.; Parvulescu, V. Catalytic hydroprocessing of lignin under thermal and ultrasound conditions. Catalysis Today. 2012, 196, 3-10.
7. Qi Song, Feng Wang, haying Cai, Yehong Wang, Junjie Zhang, Weiqiang Yu and Jie Xu, Lignin depolymerization (LDP) in alcohol over nickel based catalysts via a fragmentation—hydrogenolysis process, Energy Environ. Sci., 2013, 6, 994.
8. Buzetski, E.; Sidorova, K.; Cvengrosova, Z.; Cvengros, J. Effect of oil type on products obtained by cracking of oils and fats. Fuel Proc. Technol. 2011, 92, 2041-2047.
9. Thring et al. (Thring, R. W.; Katikaneni, S. P. R.; Bakhshi, N. N. The production of gasoline range hydrocarbons from Alcell lignin using HZSM-5 catalyst. Fuel Proc. Technol. 2000, 62, 17-30.
10. Yu, Y.; Li, X.; Su, L.; Zhang, Y.; Wang, Y.; Zhang, H. The role of shape selectivity in catalytic fast pyrolysis of lignin with zeolite catalysts. Appl. Catalysis A: General 2012, 447-448, 115-123.
11. Ma, Z.; Troussard, E.; van Bokhoven, J. A. Controlling the selectivity to chemicals from lignin via catalytic fast pyrolysis. Appl. Catalysis A: General 2012, 423-424, 130-136. 12.
12. Zhao, C.; He, J.; Lemonidou, A. A.; Li, X.; Lercher, J. A. Aqueous-phase hydrodeoxygenation of bio-derived phenols to cycloalkanes. J. Catal. 2011, 280, 8-16.
13. Zhao, Y.; Deng, L.; Liao, B.; Fu, Y.; Guo, Q.-X. Aromatics production via catalytic pyrolysis of pyrolytic lignins from bio-oil. Energy & Fuels 2010, 24, 5735-5740.
14. Valle, B.; Gayubo, A. G.; Alonso, A.; Aguayo, A. T.; Bilbao, J. Hydrothermally stable HZSM-5 zeolite catalysts for the transformation of crude bio-oil into hydrocarbons. Appl. Catal. B: Environmental B 2010, 100, 318-327.
15. Chakinala, A. G.; Chinthaginjala, J. K.; Seshan, K.; van Swaaij, W. P. M.; Kersten, S. R. A.; Brilman, D. W. F. Catalyst screening for the hydrothermal gasification of aqueous phase of bio-oil. Catal. Today 2012, 195, 83-92.
16. Takuya Yoshikawa, Taichi Yagi, Satoshi Shinohara, Tetsuya Fukunaga, Yuta Nakasaka, Teruoki Tago, Takao Masuda. Production of phenols from lignin via depolymerization and catalytic cracking. Fuel Processing Technology, 2013, 108, 69-75.
17. Yoshikawa, T. Shinohara, S.; Yagi, T.; Ryumon, N.; Nakasaka, Y.; Tago, T.; Masuda, T. Production of phenols from lignin-derived slurry liquid using iron oxide catalyst. Appl. Catal. B: Environmental 146 (2014) 289-297.
18. Yong, T.L.-K., Matsumura, Y. Reaction kinetics of the lignin conversion in supercritical water. Ind. Eng. Chem. Res. 2012, 51, 11975-11988; 19. O'Regan, J. Anaerobic digestion with supercritical water hydrolysis as pretreatment. PCT Int. Appl. (2013), WO 2013005202 A1 20130.
20. Blair J. Cox, John G. Ekerdt, Depolymerization of oak wood lignin under mild conditions using the acidic ionic liquid 1-H-3-methylimidazolium chloride as both solvent and catalyst, Bioresource Technology, 118 (2012) 584-588.
21. M. R. Sturgeon, S. Kim, K. Lawrence, R. S. Paton, S. C. Chmely, M. Nimlos, T. D. Foust, G. T. Beckham, A mechanistic investigation of acid-catalyzed cleavage of aryl-ether linkages: implications for lignin depolymerization in acidic environments, ACS Sustainable Chem. Eng., 2(2014) 472-485.
22. R. Vanholme, B. Demedts, K. Morreel, J. Ralph, and W. Boerjan, Lignin biosynthesis and structure, Plant Physiology, 153, (2010) 895-905.
23. X. Ning, H. Ishida, Phenolic materials via ring-opening polymerization: Synthesis and characterization of bisphenol-A based benzoxazines and their polymers, Journal of Polymer Science Part A: Polymer Chemistry, 32 (6) (1994) 1121-1129.
24. M. Firdaus, and M. Meier, Renewable co-polymers derived from vanillin and fatty acid derivatives, European Polymer Journal, 49(1) (2013) 156-166.
25. C. Wang, J. Sun, X. Liu, A. Sudo and T. Endo, Synthesis and copolymerization of fully bio-based benzoxazines from guaiacol, furfurylamine and stearylamine, Green Chem., 14, (2012) 2799-2806.
26. S. Kang, X. Li, J. Fan, and J. Chang, "Hydrothermal conversion of lignin: a review,"Renewable and Sustainable Energy Reviews, vol. 27, pp. 546-558, 2013.
27. Lange, H.; Decina, S.; Crestini, C. Oxidative upgrade of lignin—Recent routes reviewed. Eur. Polymer J., 2013, 49, 1151-1173.
28. Jinxing Long, Ying Xu, Tiejun Wang, Zhengqiu Yuan, Riyang Shu, Qi Zhang, Longlong Ma Efficient base-catalyzed decomposition and in situ hydrogenolysis 29. Hannelore Konnerth, Jiaguang Zhang, Ding Ma, Martin H.G. Prechtl, Ning Yan, Base promoted hydrogenolysis of lignin model compounds and organosolv lignin over metal catalysts in water, Chemical Engineering Science, Volume 123, 17 Feb. 2015, Pages 155-163.
30. M. Saisu, T. Sato, M. Watanabe, T. Adschiri, and K. Arai, "Conversion of lignin with supercritical water-phenol mixtures," Energy & Fuels, vol. 17, 922-928, 2003.
31. M. S. Wahyudiono and M. Goto, "Decomposition of lignin alkaline and chemicals recovery in sub-and supercritical water," ed: ISASF, 2004.
32. Y. Qian, C. Zuo, J. Tan, and J. He, "Structural analysis of bio-oils from sub- and supercritical water liquefaction of woody biomass," Energy, vol. 32, 196-202, (2007).
33. M. Carrier, A. Loppinet-Serani, C. Absalon, F. Marias, C. Aymonier, and M. Mench, Conversion of fern (*Pteris vittata* L.) biomass from a phytoremediation trial in sub-and supercritical water conditions, Biomass and Bioenergy, 35, (2011) 872-883.
34. R. J. Gosselink, W. Teunissen, J. E. Van Dam, E. De Jong, G. Gellerstedt, E. L. Scott, et al., Lignin depolymerisation in supercritical carbon dioxide/acetone/water fluid for the production of aromatic chemicals, Bioresource technology, 106 (2012) 173-177.
35. Yong, T. L-K.; Matsumura, Y. Kinetic analysis of lignin hydrothermal conversion in suband supercritical water. Industrial & Engineering Chemistry Research (2013), 52(16), 5626-5639.
36. Yong, T. L.-K., Matsumura, Y. Reaction kinetics of the lignin conversion in supercritical water. Ind. Eng. Chem. Res. 2012, 51, 11975-11988.
37. F. Tabasinejad, Water solubility in supercritical methane, nitrogen, and carbon dioxide: Measurement and modeling from 422 to 483 K and pressures from 3.6 to 134 MPa. Industrial & Engineering Chemistry Research (2011), 50, 4029-4041.
38. P. G. Jessop, Applications of CO2 in Homogeneous Catalysis, ChemInform, 35, (2004) 1-6.
39. S. S. Toor, Hydrothermal liquefaction of biomass: A review of subcritical water technologies. Energy (2011), 36, 2328-2342.

What is claimed is:

1. A method comprising:
producing a phenolic product or group of chemically related phenolic products by liquefaction of a biomass or lignin in the presence of a homogenous catalyst in sub-, near-, or supercritical state;
mixing one or more heterogeneous catalysts with sub-, near-, or supercritical water.

2. The method of claim 1, wherein the mixture comprises supercritical carbon dioxide.

3. The method of claim 1, wherein the mixture comprises water and supercritical carbon dioxide for selective liquefaction of biomass or lignin.

4. The method of claim 2, wherein said supercritical carbon dioxide catalyst is a green supercritical catalyst.

5. The method of claim 1, wherein said produced phenolic product or group of chemically related phenolic products do not require additional separation of the catalyst.

6. The method of claim 1, wherein one or more selective liquefaction conditions include heating to a temperature from about 200° C. to about 350° C.

7. The method of claim 1, wherein one or more selective liquefaction conditions include a minimum pressure of 72.9 atm (7.39 Mpa) for achieving a supercritical state of a homogeneous carbon dioxide catalyst.

8. The method of claim 1, wherein selective liquefaction is by batch, flow, or circulation reactors.

9. A method for selective synthesis of phenolic products by means biomass or biomass products liquefaction, comprising:
selecting in favor of at least one phenolic compound or a mixture of phenolic compounds;
synthesizing of the selected phenolic compounds from a liquid or biomass organic fraction;
producing:
said liquid or biomass organic fraction in presence of homogeneous catalyst in supercritical state;
a mixture of said homogeneous and one or more heterogeneous catalysts mixed with water in sub-critical, near-critical, or supercritical condition.

10. The method of claim 9, wherein a heterogeneous catalyst or a mixture of the heterogeneous catalysts is chosen from the group consisting of metals, metal oxides, inorganic oxides, and complex metals oxides.

11. The method of claim 10, wherein the complex metal oxides comprise perovskites, double perovskites, fluorites, and spinels.

12. The method of claim 9, wherein supercritical carbon dioxide provides selective liquefaction of lignin in presence of a heterogeneous catalyst or mixture of heterogeneous catalysts.

13. The method of claim 9, further comprising:
combining water as a sub-, near-, and supercritical fluid with a supercritical carbon dioxide catalyst in presence of a heterogeneous catalyst or a mixture of heterogeneous catalysts for selective liquefaction of biomass or lignin.

14. The method of claim 9, further comprising:
producing a phenolic product or a group of chemically related phenolic products at lower temperature.

15. The method of claim 9, wherein the supercritical carbon dioxide catalysts is a green supercritical catalysts.

16. The method of claim 9, wherein one or more selective liquefaction conditions comprise heating to a temperature from about 50° C. to about 300° C.

17. The method of claim 9, wherein one or more selective liquefaction conditions include a minimum pressure of 72.9 atm (7.39 Mpa) for providing a supercritical state of homogeneous carbon dioxide catalysts.

18. The method of claim 9, further comprising:
applying fast heating rates to the mixture.

19. The method of claim 9, further comprising:
performing selective liquefaction in batch, flow, or circulation reactors.

* * * * *